United States Patent
Hansch et al.

(10) Patent No.: US 10,815,444 B2
(45) Date of Patent: Oct. 27, 2020

(54) USE OF SPECIFIC DERIVATIVES OF QUATERNIZED NITROGEN COMPOUNDS AS ADDITIVES IN FUELS AND LUBRICANTS

(71) Applicant: BASF SE, Ludwigshafen (DE)

(72) Inventors: Markus Hansch, Speyer (DE); Harald Boehnke, Mannheim (DE); Wolfgang Grabarse, Mannheim (DE); Ludwig Voelkel, Limburgerhof (DE); Maxim Peretolchin, Lambrecht (DE)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 16/453,467

(22) Filed: Jun. 26, 2019

(65) Prior Publication Data

US 2019/0316053 A1    Oct. 17, 2019

Related U.S. Application Data

(62) Division of application No. 15/022,681, filed as application No. PCT/EP2014/069967 on Sep. 19, 2014, now Pat. No. 10,370,610.

(30) Foreign Application Priority Data

Sep. 20, 2013 (EP) ................................. 13185288
Apr. 7, 2014 (EP) ................................. 14163707

(51) Int. Cl.
*C10L 10/04*    (2006.01)
*C10L 1/22*    (2006.01)
(Continued)

(52) U.S. Cl.
CPC ............ *C10L 10/04* (2013.01); *C07C 227/14* (2013.01); *C07C 231/02* (2013.01);
(Continued)

(58) Field of Classification Search
CPC ........ C10L 10/04; C10L 1/221; C10L 1/2222; C10L 1/224; C10L 10/18; C10L 10/06;
(Continued)

(56) References Cited

U.S. PATENT DOCUMENTS 3,275,554 A    9/1966 Wagenaar
3,438,757 A    4/1969 Honnen et al.
(Continued)

FOREIGN PATENT DOCUMENTS

CA    2 803 207    12/2011
CA    2840524    * 1/2013
(Continued)

OTHER PUBLICATIONS

International Preliminary Report on Patentability dated Mar. 24, 2016, in PCT/EP2014/069967 Filed Sep. 19, 2014.
(Continued)

*Primary Examiner* — Cephia D Toomer
(74) *Attorney, Agent, or Firm* — Oblon, McClelland, Maier & Neustadt, L.L.P.

(57) ABSTRACT

The invention relates to the use of specific quaternised nitrogen compounds which are also subjected to specific transesterification or amidation, as a fuel and lubricant additive or kerosene additive, such as in particular as a detergent additive, for decreasing or preventing deposits in the injection systems of direct-injection diesel engines, in particular in common rail injection systems, for decreasing the fuel consumption of direct-injection diesel engines, in particular of diesel engines having common rail injection systems, and for minimizing the power loss in direct-injection diesel engines, in particular in diesel engines having common rail injection systems. The invention further relates to the use as an additive for petrol, in particular for operation of DISI engines.

5 Claims, 1 Drawing Sheet

(51) Int. Cl.

| | | |
|---|---|---|
| *C10L 1/222* | (2006.01) | |
| *C10L 1/224* | (2006.01) | |
| *C10L 10/18* | (2006.01) | |
| *C10M 133/06* | (2006.01) | |
| *C10M 133/16* | (2006.01) | |
| *C07C 227/14* | (2006.01) | |
| *C10L 10/06* | (2006.01) | |
| *C07C 231/02* | (2006.01) | |
| *C07C 235/86* | (2006.01) | |
| *F02M 25/14* | (2006.01) | |
| *C10N 30/08* | (2006.01) | |
| *C10N 30/00* | (2006.01) | |
| *C10N 40/25* | (2006.01) | |
| *C10N 70/00* | (2006.01) | |
| *C10N 30/04* | (2006.01) | |

(52) U.S. Cl.
CPC ............ *C07C 235/86* (2013.01); *C10L 1/221* (2013.01); *C10L 1/224* (2013.01); *C10L 1/2222* (2013.01); *C10L 10/06* (2013.01); *C10L 10/18* (2013.01); *C10M 133/06* (2013.01); *C10M 133/16* (2013.01); *F02M 25/14* (2013.01); *C10L 2200/0259* (2013.01); *C10L 2230/22* (2013.01); *C10L 2270/026* (2013.01); *C10M 2215/04* (2013.01); *C10M 2215/08* (2013.01); *C10M 2215/26* (2013.01); *C10M 2215/28* (2013.01); *C10N 2030/04* (2013.01); *C10N 2030/08* (2013.01); *C10N 2030/54* (2020.05); *C10N 2030/70* (2020.05); *C10N 2040/25* (2013.01); *C10N 2040/253* (2020.05); *C10N 2070/02* (2020.05); *Y02T 10/121* (2013.01)

(58) Field of Classification Search
CPC .......... C10L 2230/22; C10L 2270/026; C10L 2200/0259; C07C 227/14; C07C 231/02; C07C 235/86; F02M 25/14; Y02T 10/121
See application file for complete search history.

(56) References Cited

U.S. PATENT DOCUMENTS

| | | | |
|---|---|---|---|
| 3,454,555 | A | 7/1969 | Van Der Voort et al. |
| 3,565,804 | A | 2/1971 | Honnen et al. |
| 3,755,433 | A | 8/1973 | Miller et al. |
| 3,822,289 | A | 7/1974 | Clark et al. |
| 4,491,455 | A | 1/1985 | Ishizaki et al. |
| 4,832,702 | A | 5/1989 | Kummer et al. |
| 4,877,416 | A | 10/1989 | Campbell |
| 5,350,429 | A | 9/1994 | Mohr et al. |
| 5,364,419 | A | 11/1994 | Tack et al. |
| 5,492,641 | A | 2/1996 | Mohr et al. |
| 5,496,383 | A | 3/1996 | Franz et al. |
| 5,567,845 | A | 10/1996 | Franz et al. |
| 6,743,266 | B2 | 6/2004 | Derosa et al. |
| 2008/0113890 | A1 | 5/2008 | Moreton et al. |
| 2012/0138004 | A1 | 6/2012 | Stevenson et al. |

FOREIGN PATENT DOCUMENTS

| | | |
|---|---|---|
| DE | 38 26 608 A1 | 2/1990 |
| DE | 38 38 918 A1 | 5/1990 |
| DE | 41 42 241 A1 | 6/1993 |
| DE | 43 09 074 A1 | 9/1994 |
| DE | 43 19 672 A1 | 12/1994 |
| DE | 43 25 237 A1 | 2/1995 |
| DE | 196 20 262 A1 | 11/1997 |
| DE | 101 02 913 A1 | 7/2002 |
| DE | 102 43 361 A1 | 4/2004 |
| DE | 2008/060888 A2 | 5/2008 |
| EP | 0 061 895 A2 | 10/1982 |
| EP | 0 244 616 A2 | 11/1987 |
| EP | 0 261 957 A2 | 3/1988 |
| EP | 0 307 815 A1 | 3/1989 |
| EP | 0 310 875 A1 | 4/1989 |
| EP | 0 316 108 A1 | 5/1989 |
| EP | 0 356 725 A1 | 3/1990 |
| EP | 0 452 328 A1 | 10/1991 |
| EP | 0 476 485 A1 | 3/1992 |
| EP | 0 548 617 A2 | 6/1993 |
| EP | 0 639 632 A1 | 2/1995 |
| EP | 0 700 985 A1 | 3/1996 |
| EP | 0 831 141 A1 | 3/1998 |
| EP | 1 254 889 A1 | 11/2002 |
| EP | 2 033 945 A1 | 3/2009 |
| GB | 2496514 A | 5/2013 |
| JP | 62-174036 A | 7/1987 |
| WO | 87/01126 A1 | 2/1987 |
| WO | 93/18115 A1 | 9/1993 |
| WO | 94/24231 A1 | 10/1994 |
| WO | 96/03367 A1 | 2/1996 |
| WO | 96/03479 A1 | 2/1996 |
| WO | 97/03946 A1 | 2/1997 |
| WO | 98/04656 A1 | 2/1998 |
| WO | 00/44857 A2 | 8/2000 |
| WO | 00/47698 A1 | 8/2000 |
| WO | 2004/035715 A1 | 4/2004 |
| WO | 2006/135881 A2 | 12/2006 |
| WO | 2008/138836 A2 | 11/2008 |
| WO | 2013/000997 A1 | 1/2013 |
| WO | 2013/064689 A1 | 5/2013 |
| WO | 20131087701 A1 | 6/2013 |

OTHER PUBLICATIONS

Nazar-ul Islam, et al., "Electro-organic reactions. Part 27. The Mechanism of Cathodic Cleavage of Activated Esters; Oxalates, Squarates, and Oxamates," Tetrahedron, vol. 43, No. 5, 1987 (12 pages) XP055153037.

International Search Report dated Nov. 28, 2014, in PCT/EP2014/069967 Filed Sep. 19, 2014.

* cited by examiner

| step | duration (minutes) | engine speed (rpm) +/- 20 | load (%) | torque (Nm) +/-5 | boost air after IC (°C) +/-3 |
|---|---|---|---|---|---|
| 1 | 2' | 1750 | (20) | 62 | 45 |
| 2 | 7' | 3000 | (60) | 173 | 50 |
| 3 | 2' | 1750 | (20) | 62 | 45 |
| 4 | 7' | 3500 | (80) | 212 | 50 |
| 5 | 2' | 1750 | (20) | 62 | 45 |
| 6 | 10' | 4000 | 100 | * | 50 |
| 7 | 2' | 1250 | (10) | 25 | 43** |
| 8 | 7' | 3000 | 100 | * | 50 |
| 9 | 2' | 1250 | (10) | 25 | 43** |
| 10 | 10' | 2000 | 100 | * | 50 |
| 11 | 2' | 1250 | (10) | 25 | 43** |
| 12 | 7' | 4000 | 100 | * | 50 |
| | Σ= 1 hour | | | | |
\* for expected range see appendix 06.5
\*\* target only
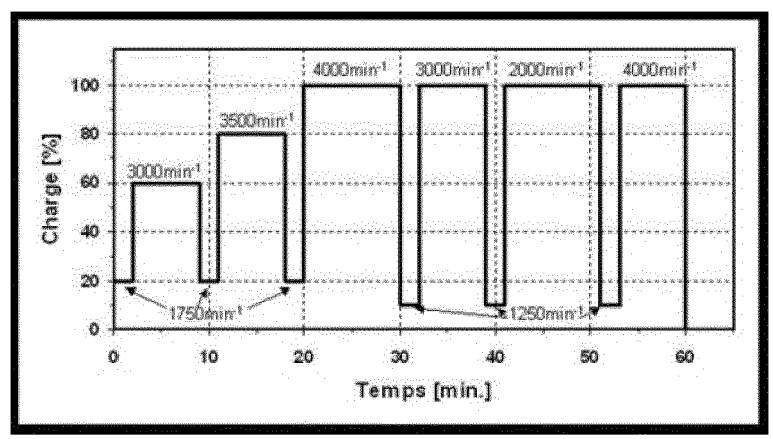

USE OF SPECIFIC DERIVATIVES OF QUATERNIZED NITROGEN COMPOUNDS AS ADDITIVES IN FUELS AND LUBRICANTS

CROSS REFERENCE TO RELATED APPLICATIONS

The present application is a Divisional of U.S. application Ser. No. 15/022,681, filed on Mar. 17, 2016, which is a 35 U.S.C. § 371 national stage patent application of International patent application no. PCT/EP2014/069967, filed on Sep. 19, 2014, the text of which is incorporated by reference, and claims the benefit of the filing date of EP application nos. 14163707.4, filed on Apr. 7, 2014, and 13185288.1, filed on Sep. 20, 2013, the text of which is also incorporated by reference.

The present invention relates to the use of specific quaternized nitrogen compounds which have additionally been subjected to a specific transesterification or amidation as a fuel additive and lubricant additive, such as, more particularly, as a detergent additive; for reducing or preventing deposits in the injection systems of direct injection diesel engines, especially in common rail injection systems, for reducing the fuel consumption of direct injection diesel engines, especially of diesel engines with common rail injection systems, and for minimizing power loss in direct injection diesel engines, especially in diesel engines with common rail injection systems; and as an additive for gasoline fuels, especially for operation of DISI engines.

STATE OF THE ART

In direct injection diesel engines, the fuel is injected and distributed ultrafinely (nebulized) by a multihole injection nozzle which reaches directly into the combustion chamber of the engine, instead of being introduced into a prechamber or swirl chamber as in the case of the conventional (chamber) diesel engine. The advantage of direct injection diesel engines lies in their high performance for diesel engines and nevertheless low fuel consumption. Moreover, these engines achieve a very high torque even at low speeds.

At present, essentially three methods are being used for injection of the fuel directly into the combustion chamber of the diesel engine: the conventional distributor injection pump, the pump-nozzle system (unit-injector system or unit-pump system), and the common rail system.

In the common rail system, the diesel fuel is conveyed by a pump with pressures up to 2000 bar into a high-pressure line, the common rail. Proceeding from the common rail, branch lines run to the different injectors which inject the fuel directly into the combustion chamber. The full pressure is always applied to the common rail, which enables multiple injection or a specific injection form. In the other injection systems, in contrast, only a smaller variation in the injection is possible. Injection in the common rail is divided essentially into three groups: (1.) pre-injection, by which essentially softer combustion is achieved, such that harsh combustion noises ("nailing") are reduced and the engine seems to run quietly; (2.) main injection, which is responsible especially for a good torque profile; and (3.) post-injection, which especially ensures a low $NO_x$ value. In this post-injection, the fuel is generally not combusted, but instead vaporized by residual heat in the cylinder. The exhaust gas/fuel mixture formed is transported to the exhaust gas system, where the fuel, in the presence of suitable catalysts, acts as a reducing agent for the nitrogen oxides $NO_x$.

The variable, cylinder-individual injection in the common rail injection system can positively influence the pollutant emission of the engine, for example the emission of nitrogen oxides ($NO_x$), carbon monoxide (CO) and especially of particulates (soot). This makes it possible, for example, for engines equipped with common rail injection systems to meet the Euro 4 standard theoretically even without additional particulate filters.

In modern common rail diesel engines, under particular conditions, for example when biodiesel-containing fuels or fuels with metal impurities such as zinc compounds, copper compounds, lead compounds and other metal compounds are used, deposits can form on the injector orifices, which adversely affect the injection performance of the fuel and hence impair the performance of the engine, i.e. especially reduce the power, but in some cases also worsen the combustion. The formation of deposits is enhanced further by further developments in the injector construction, especially by the change in the geometry of the nozzles (narrower, conical orifices with rounded outlet). For lasting optimal functioning of engine and injectors, such deposits in the nozzle orifices must be prevented or reduced by suitable fuel additives.

In the injection systems of modern diesel engines, deposits cause significant performance problems. It is common knowledge that such deposits in the spray channels can lead to a decrease in the fuel flow and hence to power loss. Deposits at the injector tip, in contrast, impair the optimal formation of fuel spray mist and, as a result, cause worsened combustion and associated higher emissions and increased fuel consumption. In contrast to these conventional "external" deposition phenomena, "internal" deposits (referred to collectively as internal diesel injector deposits (IDID)) in particular parts of the injectors, such as at the nozzle needle, at the control piston, at the valve piston, at the valve seat, in the control unit and in the guides of these components, also increasingly cause performance problems. Conventional additives exhibit inadequate action against these IDIDs.

EP-A-2 033 945 discloses cold flow improvers which are prepared by quaternizing specific tertiary monoamines bearing at least one $C_8$-$C_{40}$-alkyl radical with a $C_1$-$C_4$-alkyl ester of specific carboxylic acids. Examples of such carboxylic esters are dimethyl oxalate, dimethyl maleate, dimethyl phthalate and dimethyl fumarate. Uses other than that for improvement of the CFPP value of middle distillates are not demonstrated in EP-A-2 033 945.

Quaternary ammonium salts of alpha-hydroxycarboxylic acids are proposed in EP-A-1 254 889 as cleaning agents for electronic components.

In addition, Japanese patent application, application number 61-012197, describes the use of quaternary ammonium salts of organic carboxylic acids as surfactants or raw materials for medicaments or cosmetics.

GB-A-2496514 describes alkyl-substituted ammonium compounds, prepared by quaternization by means of various conventional quaternizing agents such as, more particularly, chlorides, nitrates and acetates, and the use thereof as a fuel additive. The use of fully esterified polycarboxylic acid polyalkyl esters is not disclosed therein.

The applicant's WO2013/087701 discloses quaternized alkylamines and fuel compositions and lubricant compositions additized therewith, wherein the quaternizing agents proposed are, for example, dicarboxylic esters. However, the compounds known from the prior art still have disadvantages in relation to handling, storage stability and motor oil compatibility.

The problem addressed was therefore that of providing improved fuel additives which no longer have the disadvantages described above but still effectively prevent deposits in direct injection or indirect injection diesel engines, such as, more particularly, deposits in the injector tip and internal injector deposits in the course of operation of common rail diesel engines.

BRIEF DESCRIPTION OF THE INVENTION

It has now been found that, surprisingly, the above object is achieved by providing specific derivatives of nitrogen compounds, for example alkylamines, quaternized with polycarboxylic esters, and fuel compositions and lubricant compositions additized therewith.

Surprisingly, the inventive additives, as illustrated especially by the appended use examples, can be handled surprisingly efficiently, have surprisingly good motor oil compatibility, and also have excellent efficacy in direct injection and indirect injection diesel engines, such as, more particularly, as an additive for reducing power loss and reduction of internal deposits.

DESCRIPTION OF FIGURES

FIG. 1 shows the running of a one-hour engine test cycle according to CEC F-098-08.

DETAILED DESCRIPTION OF THE INVENTION

A1) Specific Embodiments

The present invention relates especially to the following specific embodiments:
1. The use of a reaction product comprising a quaternized nitrogen compound or of a fraction thereof which comprises a quaternized nitrogen compound and is obtained from the reaction product by purification, said reaction product being obtainable by
   a) reacting a quaternizable nitrogen compound, for example a quaternizable alkylamine comprising at least one quaternizable, especially tertiary, amino group with a quaternizing agent which converts the at least one quaternizable, especially tertiary, amino group to a quaternary ammonium group, the quaternizing agent being the especially polyesterified, preferably fully esterified, alkyl ester, such as, more particularly, lower alkyl ester, for example ester having one or more straight-chain or branched $C_{1-4}$-alkyl radicals and particularly methyl or ethyl radicals, of an aliphatic, cycloaromatic or cycloaliphatic, especially aliphatic, polycarboxylic acid, especially of a dicarboxylic acid, such as, more particularly the methyl or ethyl ester of a cycloaliphatic or aliphatic, more particularly aliphatic, dicarboxylic acid; and
   b) transesterifying or amidating the remaining ester group of the quaternization product from stage a) (also referred to in the present document as quaternized polycarboxylic ester; or quaternized ammonium salt of a polycarboxylic ester);
   as a fuel additive or lubricant additive;
   where particularly the transesterified or amidated form (i.e. the product from stage b)) of the quaternization product (i.e. the product from stage a)) has more hydrophobic character than prior to the transesterification or prior to the amidation, which further improves especially the oil solubility of the products thus obtained.
   This can be achieved, for example, by using alcohols or amines having a higher number of carbon atoms than the ester radical of the original quaternization product from stage a) which has been removed by the esterification or amidation.
   For example, it is possible by the transesterification by means of an alcohol bearing a long-chain hydrocarbyl radical as defined herein, or by amidation with a primary or secondary, especially primary, amine bearing at least one long-chain hydrocarbyl radical as defined herein, to introduce suitable longer-chain radicals into the quaternization product.
   More particularly, in accordance with the invention, the transesterification or amidation replaces at least one lower alkyl ester group, especially methyl or ethyl ester group, with an ester group having a longer-chain hydrocarbyl radical or with an amido group having at least one longer-chain hydrocarbyl radical in the quaternization product from stage a); as achievable especially by transesterification (with suitable mono- or polyols, polyalkoxylates, polyol-started polyalkoxylates, polyethers and polyalkylene alcohols such as polyisobutylene alcohols), or amidation (with suitable long-chain mono- or polyamines or polyalkyleneamines, for example polyisobutyleneamine (PIBA)), as elucidated, for example, in section A5) which follows.
   For example, it is possible to replace a methyl or ethyl group in the ester function of the quaternization product from stage a) with a longer-chain radical, for example a long-chain hydrocarbyl radical defined herein and having 5 to 50 or 8 to 50 carbon atoms in a long-chain alcohol, or another radical in a co-reactant capable of transesterification or amidation (alcohol or amine), as defined in detail in section A5) which follows.
   A further suitable criterion for selection of a number of groups which can be introduced in accordance with the invention by transesterification or amidation into the quaternization product of stage a) is the partition coefficient ("log Pow"; or "log P") the compounds used with preference for transesterification or amidation (alcohols and amines; such as, more particularly, the compound classes described in section A5)). This log Pow or log P value of suitable compounds is usually greater than 0.7, especially greater than 0.8, greater than 0.9, greater than 1, or greater than 1.1, and has no upper limit in principle, provided that the additive properties are not adversely affected as a result and/or the oil solubility of the additive is improved as a result. For example, the value may be within a range from 1.2 to 30, 1.3 to 25, 1.3 to 20 or 1.3 to 15 or 1.3 to 13 or 2 to 10 or 2 to 5.
2. The use according to embodiment 1 as an additive for reducing the fuel consumption of direct injection diesel engines, especially of diesel engines with common rail injection systems, and/or for minimizing power loss in direct injection diesel engines, especially in diesel engines with common rail injection systems, such as, more particularly, power loss resulting from metals such as Zn, Na and/or K and compounds comprising these metals, such as salts thereof.
3. The use according to embodiment 1 as a gasoline fuel additive for reducing the level of deposits in the intake system of a gasoline engine, such as, more particularly, DISI (direct injection spark ignition) and PFI (port fuel injector) engines.

4. The use according to embodiment 1 as a diesel fuel additive for reducing and/or preventing deposits in the intake systems, such as especially the internal diesel injector deposits (IDIDs), and/or valve sticking in direct injection diesel engines, especially in common rail injection systems.

5. The use according to any of the preceding embodiments, wherein the quaternizable nitrogen compound is selected from:
   a) at least one alkylamine of the following general formula 3:

$$R_aR_bR_cN \quad (3)$$

in which
   at least one of the $R_a$, $R_b$ and $R_c$ radicals, for example 1 or 2 of the radicals, is a straight-chain or branched, saturated or unsaturated $C_8$-$C_{40}$-hydrocarbyl radical (especially straight-chain or branched $C_8$-$C_{40}$-alkyl) and the other radicals are identical or different, straight-chain or branched, saturated or unsaturated $C_1$-$C_6$-hydrocarbyl radicals (especially $C_1$-$C_6$-alkyl); or
   in which all the $R_a$, $R_b$ and $R_c$ radicals are identical or different, straight-chain or branched, saturated or unsaturated $C_8$-$C_{40}$-hydrocarbyl radicals, especially straight-chain or branched $C_8$-$C_{40}$-alkyl radicals.
   b) at least one polyalkene-substituted amine comprising at least one quaternizable, especially tertiary, amino group;
   c) at least one polyether-substituted amine comprising at least one quaternizable, especially tertiary, amino group; and
   d) at least one reaction product of a hydrocarbyl-substituted acylating agent and a compound comprising a nitrogen or oxygen atom and additionally comprising at least one quaternizable amino group; and
   e) mixtures thereof.

6. The use according to any of embodiments 1 to 5, wherein the quaternizing agent is a compound of the general formula 2

$$R_1OC(O)\text{-}A\text{-}C(O)OR_{1a} \quad (2)$$

in which
   $R_1$ and $R_{1a}$ are each independently a lower alkyl radical, more particularly a straight-chain or branched $C_{1-4}$-alkyl radical, more particularly methyl or ethyl radical, and
   A is a chemical bond (i.e. carbon-carbon single bond) or an optionally mono- or polysubstituted, for example mono-, di-, tri- or tetrasubstituted, hydrocarbylene such as, more particularly, an optionally mono- or polysubstituted, for example di-, tri- or tetrasubstituted, alkylene or alkenylene, or an optionally substituted monocyclic arylene, especially phenylene, or cycloalkylene, especially cyclopentylene and cyclohexylene, radical. Substituents for group A are, for example, selected from keto groups, —COOH, —COO-alkyl, especially COO-lower alkyl, —OH, —SH, —CN, amino, —NO₂, alkyl, especially $C_1$-$C_6$ alkyl, or alkenyl, especially $C_2$-$C_6$-alkenyl, groups.

7. The use according to any of the preceding embodiments, wherein, in stage b), the transesterification of the remaining ester group of the quaternization product of stage a) (i.e. of the quaternized polycarboxylic ester or of the quaternized ammonium salt of a polycarboxylic ester) is effected by reaction with at least one saturated or unsaturated linear, branched or cyclic aliphatic mono- or polyol, a polyalkoxylate, an alcohol-started polyalkoxylate or (especially hydroxyl-terminated) polyether; or wherein the amidation in stage b) of the remaining ester group of the quaternization product of stage a) (i.e. of the quaternized polycarboxylic ester or of the quaternized ammonium salt of a polycarboxylic ester) is effected by reaction with at least one saturated or unsaturated linear, branched or cyclic aliphatic primary or secondary mono- or polyamine;
where especially the transesterified or amidated form has more hydrophobic character, i.e. a higher proportion of carbon atoms.

8. The use according to any of the preceding embodiments, wherein the quaternizable tertiary amine is a compound of the formula 3 in which at least two of the $R_a$, $R_b$ and $R_c$ radicals are the same or different and are each a straight-chain or branched $C_{10}$-$C_{20}$-alkyl radical and the other radical is $C_1$-$C_4$-alkyl.

9. The use according to any of the preceding embodiments, wherein the quaternizing agent is selected from di-$C_1$-$C_4$-alkyl phthalates and di-$C_1$-$C_4$-alkyl, more particularly dimethyl or diethyl, oxalates.

10. The use according to any of the preceding embodiments, wherein the fuel is selected from diesel fuels, biodiesel fuels, gasoline fuels, and alkanol-containing gasoline fuels.

11. A quaternized nitrogen compound as defined in any of embodiments 1 to 10.

12. A process for preparing a quaternized nitrogen compound according to embodiment 11, comprising
   a) the reaction a quaternizable nitrogen compound as defined above, for example of a quaternizable alkylamine comprising at least one quaternizable tertiary amino group with a quaternizing agent which converts the at least one tertiary amino group to a quaternary ammonium group, the quaternizing agent being the (especially fully esterified) alkyl ester of an aliphatic, cycloaromatic or cycloaliphatic polycarboxylic acid, especially of a dicarboxylic acid; and
   b) the transesterification or amidation of the remaining ester group of the quaternization product of stage a) (i.e. of the quaternized polycarboxylic ester or of the quaternized ammonium salt of a polycarboxylic ester);
   where the transesterified or amidated form especially has more hydrophobic character and has, for example, a higher proportion of carbon atoms, as defined above.

13. An additive concentrate comprising, in combination with further diesel fuel additives or gasoline fuel additives or lubricant additives, at least one quaternized nitrogen compound as defined in embodiment 11 or prepared according to embodiment 12.

14. A fuel composition or lubricant composition comprising, in a majority of a customary fuel or lubricant i.e. a fuel or lubricant which is customary on the market and which optionally already comprises other customary additives as described herein, but not a quaternization product of the invention as defined above, an effective proportion (i.e. one which brings about the desired additive effect) (for example 10 to 5000 ppm by weight, preferably 20 to 1500 ppm by weight, especially 25 to 1000 ppm by weight, particularly 30 to 750 ppm by weight, based in each case on the total amount of fuel or lubricant) of at least one reaction product comprising a quaternized nitrogen compound, or a fraction thereof which comprises a quaternized nitrogen compound and is obtained from the reaction product by purification, said reaction product being obtainable by
a) the reaction a quaternizable nitrogen compound as defined above, for example of a quaternizable alkylamine comprising at least one quaternizable tertiary amino group, with a quaternizing agent which converts the at least one tertiary amino group to a quaternary ammonium group, the quaternizing agent being the (especially fully esterified) alkyl ester of an aliphatic, cycloaromatic or cycloaliphatic polycarboxylic acid, especially of a dicarboxylic acid; and
b) the transesterification or amidation of the remaining ester group of the quaternization product of stage a) (i.e. of the quaternized polycarboxylic ester or of the quaternized ammonium salt of a polycarboxylic ester);
where the transesterified or amidated form especially has more hydrophobic character and has, for example, a higher proportion of carbon atoms, as defined above.

15. The fuel composition or lubricant composition according to embodiment 14, wherein the quaternizable nitrogen compound is selected from
a) at least one alkylamine of the above general formula 3
b) at least one polyalkene-substituted amine comprising at least one quaternizable, especially tertiary, amino group;
c) at least one polyether-substituted amine comprising at least one quaternizable, especially tertiary, amino group; and
d) at least one reaction product of a hydrocarbyl-substituted acylating agent and a compound comprising a nitrogen or oxygen atom and additionally comprising at least one quaternizable amino group; and
e) mixtures thereof.

16. The fuel composition or lubricant composition according to either of embodiments 14 and 15, wherein the quaternizing agent is a compound of the above general formula 2

17. The fuel composition or lubricant composition according to any of embodiments 14 to 16,
wherein the transesterification in stage b) of the remaining ester group of the quaternization product of stage a) (i.e. of the quaternized polycarboxylic ester or of the quaternized ammonium salt of a polycarboxylic ester) is effected by reaction with at least one saturated or unsaturated linear, branched or cyclic aliphatic mono- or polyol, a polyalkoxylate, an alcohol-started polyalkoxylate or (especially hydroxyl-terminated) polyether;
or wherein
the amidation in stage b) of the remaining ester group of the quaternization product of stage a) (i.e. of the quaternized polycarboxylic ester or of the quaternized ammonium salt of a polycarboxylic ester) is effected by reaction with at least one saturated or unsaturated linear, branched or cyclic aliphatic primary or secondary mono- or polyamine;
where the transesterified or amidated form especially has more hydrophobic character and has, for example, a higher proportion of carbon atoms, as defined above.

18. The fuel composition or lubricant composition according to any of embodiments 14 to 17, wherein the quaternizable tertiary amine is a compound of the formula 3 in which at least two of the $R_a$, $R_b$ and $R_c$ radicals are the same or different and are each a straight-chain or branched $C_{10}$-$C_{20}$-alkyl radical and the other radical is $C_1$-$C_4$-alkyl.

19. The fuel composition or lubricant composition according to any of embodiments 14 to 18, wherein the quaternizing agent is selected from di-$C_1$-$C_4$-alkyl phthalates and di-$C_1$-$C_4$-alkyl, more particularly dimethyl or diethyl, oxalates.

Test methods suitable in each case for testing the above-designated applications are known to those skilled in the art, or are described in the experimental section which follows, to which general reference is hereby explicitly made.

A2) General Definitions

In the absence of statements to the contrary, the following general conditions apply:

"Quaternizable" nitrogen groups or amino groups comprise especially primary, secondary and, in particular, tertiary amino groups.

"Hydrocarbyl" should be interpreted broadly and comprises both long-chain and short-chain, straight-chain and branched hydrocarbyl radicals having 1 to 50 carbon atoms, which may optionally additionally comprise heteroatoms, for example O, N, NH, S, in the chain thereof. A specific group of hydrocarbyl radicals comprises both long-chain and short-chain, straight-chain or branched alkyl radicals having 1 to 50 carbon atoms.

"Long-chain" or "high molecular" weight hydrocarbyl radicals are straight-chain or branched hydrocarbyl radicals and have 5 to 50 or 6 to 50 or 7 to 50 or 8 to 50 or 8 to 40 or 10 to 20 carbon atoms, which may optionally additionally comprise heteroatoms, for example O, N, NH, S, in the chain thereof. In addition, the radicals may be mono- or polyunsaturated and have one or more noncumulated, for example 1 to 5, such as 1, 2 or 3, C—C double bonds or C—C triple bonds, especially 1, 2 or 3 double bonds. They may be of natural or synthetic origin.

They may also have a number-average molecular weight (Mn) of 85 to 20000, for example 113 to 10000, or 200 to 10 000 or 350 to 5000, for example 350 to 3000, 500 to 2500, 700 to 2500, or 800 to 1500. In that case, they are more particularly formed essentially from C2-6, especially C2-4, monomer units such as ethylene, propylene, n- or isobutylene or mixtures thereof, where the different monomers may be copolymerized in random distribution or as blocks. Such long-chain hydrocarbyl radicals are also referred to as polyalkylene radicals or poly-C2-6- or poly-C2-4-alkylene radicals. Suitable long-chain hydrocarbyl radicals and the preparation thereof are also described, for example, in WO 2006/135881 and the literature cited therein.

Examples of particularly useful polyalkylene radicals are polyisobutenyl radicals derived from what are called "high-reactivity" polyisobutenes which feature a high content of terminal double bonds. Terminal double bonds are alpha-olefinic double bonds of the type

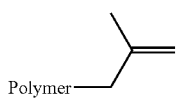

which are also referred to collectively as vinylidene double bonds. Suitable high-reactivity polyisobutenes are, for example, polyisobutenes which have a proportion of vinylidene double bonds of greater than 70 mol %, especially greater than 80 mol % or greater than 85 mol %. Preference is given especially to polyisobutenes which have homogeneous polymer skeletons. Homogeneous polymer skeletons are possessed especially by those polyisobutenes formed from isobutene units to an extent of at least 85% by weight, preferably to an extent of at least 90% by weight and more preferably to an extent of at least 95% by weight. Such high-reactivity polyisobutenes preferably have a number-average molecular weight within the abovementioned range. In addition, the high-reactivity polyisobutenes may have a polydispersity in the range from 1.05 to 7, especially of about 1.1 to 2.5, for example of less than 1.9 or less than 1.5. Polydispersity is understood to mean the quotient of weight-average molecular weight Mw divided by the number-average molecular weight Mn.

Particularly suitable high-reactivity polyisobutenes are, for example, the Glissopal brands from BASF SE, especially Glissopal® 1000 (Mn=1000), Glissopal® V 33 (Mn=550), and Glissopal® 2300 (Mn=2300), and mixtures thereof. Other number-average molecular weights can be established in a manner known in principle by mixing polyisobutenes of different number-average molecular weights or by extractive enrichment of polyisobutenes of particular molecular weight ranges.

A specific group of long-chain hydrocarbyl radicals comprises straight-chain or branched alkyl radicals ("long-chain alkyl radicals") having 8 to 50, for example 8 to 40 or 8 to 30 or 10 to 20, carbon atoms.

"Short-chain hydrocarbyl" or "low molecular weight hydrocarbyl" is especially straight-chain or branched alkyl or alkenyl, optionally interrupted by one or more, for example 2, 3 or 4, heteroatom groups such as —O— or —NH—, or optionally mono- or polysubstituted, for example di-, tri- or tetrasubstituted.

"Hydrocarbylene" represents straight-chain or singly or multiply branched bridge groups having 1 to 10 carbon atoms, optionally interrupted by one or more, for example 2, 3 or 4, heteroatom groups such as —O— or —NH—, or optionally mono- or polysubstituted, for example di-, tri- or tetrasubstituted.

"Alkyl" or "lower alkyl" represents especially saturated, straight-chain or branched hydrocarbon radicals having 1 to 4, 1 to 5, 1 to 6, or 1 to 7, carbon atoms, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; and also n-heptyl, and the singly or multiply branched analogs thereof.

"Long-chain alkyl" especially represents saturated straight-chain or branched hydrocarbyl radicals having 8 to 50, for example 8 to 40 or 8 to 30 or 10 to 20, carbon atoms, such as octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, squalyl, constitutional isomers, especially singly or multiply branched isomers and higher homologs thereof.

"Hydroxyalkyl" represents especially the mono- or polyhydroxylated, especially monohydroxylated, analogs of the above alkyl radicals, for example the monohydroxylated analogs of the above straight-chain or branched alkyl radicals, for example the linear hydroxyalkyl groups, for example those having a primary (terminal) hydroxyl group, such as hydroxymethyl, 2-hydroxyethyl, 3-hydroxypropyl, 4-hydroxybutyl, or those having nonterminal hydroxyl groups, such as 1-hydroxyethyl, 1- or 2-hydroxypropyl, 1- or 2-hydroxybutyl or 1-, 2- or 3-hydroxybutyl.

"Alkenyl" represents mono- or polyunsaturated, especially monounsaturated, straight-chain or branched hydrocarbyl radicals having 2 to 4, 2 to 6, or 2 to 7 carbon atoms and one double bond in any position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Hydroxyalkenyl" represents especially the mono- or polyhydroxylated, especially monohydroxylated, analogs of the above alkenyl radicals.

"Aminoalkyl" and "aminoalkenyl" represent especially the mono- or polyaminated, especially monoaminated, analogs of the above alkyl and alkenyl radicals respectively, or analogs of the above hydroxyalkyl where the OH group has been replaced by an amino group.

"Alkylene" represents straight-chain or singly or multiply branched hydrocarbyl bridging groups having 1 to 10 carbon atoms, for example $C_1$-$C_7$-alkylene groups selected from
—CH$_2$—, —(CH$_2$)$_2$—, —(CH$_2$)$_3$—, —CH$_2$—CH(CH$_3$)—, —CH(CH$_3$)—CH$_2$—, —(CH$_2$)$_4$—, —(CH$_2$)$_2$—CH(CH$_3$)—,
—CH$_2$—CH(CH$_3$)—CH$_2$—, (CH$_2$)$_4$—, —(CH$_2$)$_5$—, —(CH$_2$)$_6$—, —(CH$_2$)$_7$—, —CH(CH$_3$)—CH$_2$—CH$_2$—CH(CH$_3$)— and —CH(CH$_3$)—CH$_2$—CH$_2$—CH$_2$—CH(CH$_3$)— or $C_1$-$C_4$-alkylene groups selected from —CH$_2$—, —(CH$_2$)$_2$—, —(CH$_2$)$_3$—, —CH$_2$—CH(CH$_3$)—,
—CH(CH$_3$)—CH$_2$—, —(CH$_2$)$_4$—, —(CH$_2$)$_2$—CH(CH$_3$)—, —CH$_2$—CH(CH$_3$)—CH$_2$—.

or $C_2$-$C_6$-alkylene groups, for example
—CH$_2$—CH(CH$_3$)—, —CH(CH$_3$)—CH$_2$—, —CH(CH$_3$)—CH(CH$_3$)—, —C(CH$_3$)$_2$—CH$_2$—, —CH$_2$—C(CH$_3$)$_2$—,
—C(CH$_3$)$_2$—CH(CH$_3$)—, —CH(CH$_3$)—C(CH$_3$)$_2$—, —CH$_2$—CH(Et)-, —CH(CH$_2$CH$_3$)—CH$_2$—,
—CH(CH$_2$CH$_3$)—CH(CH$_2$CH$_3$)—, —C(CH$_2$CH$_3$)$_2$—CH$_2$—, —CH$_2$—C(CH$_2$CH$_3$)$_2$—,
—CH$_2$—CH(n-propyl)-, —CH(n-propyl)-CH$_2$—, —CH(n-propyl)-CH(CH$_3$)—, —CH$_2$—CH(n-butyl)-, —CH(n-butyl)-CH$_2$—, —CH(CH$_3$)—CH(CH$_2$CH$_3$)—, —CH(CH$_3$)—CH(n-propyl)-, —CH(CH$_2$CH$_3$)—CH(CH$_3$)—, —CH(CH$_3$)—CH(CH$_2$CH$_3$)—, or C$_2$-C$_4$-alkylene groups, for example selected from —(CH$_2$)$_2$—, —CH$_2$—CH(CH$_3$)—, —CH(CH$_3$)—CH$_2$—, —CH(CH$_3$)—CH(CH$_3$)—, —C(CH$_3$)$_2$—CH$_2$—, —CH$_2$—C(CH$_3$)$_2$—, —CH$_2$—CH(CH$_2$CH$_3$)—, —CH(CH$_2$CH$_3$)—CH$_2$—.

Oxyalkylene radicals correspond to the definition of the above straight-chain or singly or multiply branched alkylene radicals having 2 to 10 carbon atoms, where the carbon chain may be interrupted once or more than once, especially once, by an oxygen heteroatom. Nonlimiting examples include: —CH$_2$—O—CH$_2$—, —(CH$_2$)$_2$—O—(CH$_2$)$_2$—, —(CH$_2$)$_3$—O—(CH$_2$)$_3$—, or —CH$_2$—O—(CH$_2$)$_2$—, —(CH$_2$)$_2$—O—(CH$_2$)$_3$—, —CH$_2$—O—(CH$_2$)$_3$ "Aminoalkylene" corresponds to the definition of the above straight-chain or singly or multiply branched alkylene radicals having 2 to 10 carbon atoms, where the carbon chain may be interrupted once or more than once, especially once, by a nitrogen group (especially —NH— group). Nonlimiting examples include: —CH$_2$—NH—CH$_2$—, —(CH$_2$)$_2$—NH—(CH$_2$)$_2$—, —(CH$_2$)$_3$—NH—(CH$_2$)$_3$—, or —CH$_2$—NH—(CH$_2$)$_2$—, —(CH$_2$)$_2$—NH—(CH$_2$)$_3$—, —CH$_2$—NH—(CH$_2$)$_3$.

"Alkenylene" represents the mono- or polyunsaturated, especially monounsaturated, analogs of the above alkylene groups having 2 to 10 carbon atoms, especially C$_2$-C$_7$-alkenylenes or C$_2$-C$_4$-alkenylene, such as —CH=CH—, —CH=CH—CH$_2$—, —CH$_2$—CH=CH—, —CH=CH—CH$_2$—CH$_2$—, —CH$_2$—CH=CH—CH$_2$—, —CH$_2$—CH$_2$—CH=CH—, —CH(CH$_3$)—CH=CH—, —CH$_2$—C(CH$_3$)=CH—.

"Cycloalkyl" represents carbocyclic radicals having 3 to 20 carbon atoms, for example C$_3$-C$_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl, cycloheptyl, and also to cyclopropylmethyl, cyclopropylethyl, cyclobutylmethyl, cyclobutylethyl, cyclopentylmethyl, cyclopentylethyl, cyclohexylmethyl, or C$_3$-C$_7$-cycloalkyl such as cyclopropyl, cyclobutyl, cyclopentyl, cyclohexyl, cycloheptyl, cyclopropylmethyl, cyclopropylethyl, cyclobutylmethyl, cyclopentylethyl, cyclohexylmethyl, where the bond to the rest of the molecule may be via any suitable carbon atom.

"Cycloalkenyl" or mono- or polyunsaturated cycloalkyl represents especially monocyclic, mono- or polyunsaturated hydrocarbyl groups having 5 to 8, preferably to 6, carbon ring members, for example the monounsaturated radicals cyclopenten-1-yl, cyclopenten-3-yl, cyclohexen-1-yl, cyclohexen-3-yl and cyclohexen-4-yl.

"Cycloalkylene" represents twin-bonded analogs of the above carbocyclic cycloalkyl radicals having 3 to 20 carbon atoms, for example C$_3$-C$_{12}$-cycloalkylene, where the bond to the rest of the molecule may be via any suitable carbon atom. Examples are cyclopropylene, cyclobutylene, cyclopentylene, cyclohexylene, cycloheptylene and cyclooctylene.

"Aryl" represents mono- or polycyclic, preferably mono- or bicyclic, optionally substituted aromatic radicals having 6 to 20, for example 6 to 10, ring carbon atoms, for example phenyl, biphenyl, naphthyl such as 1- or 2-naphthyl, tetrahydronaphthyl, fluorenyl, indenyl and phenanthrenyl. These aryl radicals may optionally bear 1, 2, 3, 4, 5 or 6 identical or different substituents.

"Alkylaryl" represents analogs of the above aryl radicals mono- or polyalkyl-substituted, especially mono- or dialkyl-substituted, in any ring position, where aryl is likewise as defined above, for example C$_1$-C$_4$-alkylphenyl, where the C$_1$-C$_4$-alkyl radicals may be in any ring position.

"Substituents" for radicals specified herein are especially, unless stated otherwise, selected from keto groups, —COOH, —COO-alkyl, —OH, —SH, —CN, amino, —NO$_2$, alkyl, especially C$_1$-C$_6$ alkyl, or alkenyl, especially C$_2$-C$_6$-alkenyl, groups.

"Mn" represents the number-average molecular weight and is determined in a conventional manner; more particularly, such figures relate to Mn values determined by relative methods, such as gel permeation chromatography with THF as the eluent and polystyrene standards, or absolute methods, such as vapor phase osmometry using toluene as the solvent.

"Mw" represents the weight-average molecular weight and is determined in a conventional manner; more particularly, such figures relate to Mw values determined by relative methods, such as gel permeation chromatography with THF as the eluent and polystyrene standards, or absolute methods, such as light scattering.

The "degree of polymerization" usually refers to the numerical mean degree of polymerization (determination method: gel permeation chromatography with THF as the eluent and polystyrene standards; or GC-MS coupling).

The partition coefficient is determined by means of various methods according to the value. The partition coefficient "log Pow" of a compound up to a value of about 6 can be determined in accordance with OECD Guideline 117 at 25° C. in n-octanol/water; by this method, n-butanol has a value of 1, pentanol a value of 1.3 or 2-ethylhexanol a value of 2.9.

Higher partition coefficients (i.e. value >6); referred to here as "log P") are determined by the ACD/log P method (Perauskas, A. A. et al., Perspectives in Drug Discovery and Design, 19: 99-116 (2000).

A3) Quaternizable Nitrogen Compounds

Quaternizable nitrogen compounds are especially:
A3.1) Tertiary Amines
Tertiary amines are especially compounds of the above formula 3 and are compounds known per se, as described, for example, in EP-A-2 033 945.

The tertiary amine reactant 3 preferably bears a segment of the formula NR$_a$R$_b$ where one of the radicals has an alkyl group having 8 to 40 carbon atoms and the other an alkyl group having up to 40 and more preferably 8 to 40 carbon atoms. The R$_c$ radical is especially a short-chain C$_1$-C$_6$-alkyl radical, such as a methyl, ethyl or propyl group. R$_a$ and R$_b$ may be straight-chain or branched, and/or may be the same or different. For example, R$_a$ and R$_b$ may be a straight-chain C$_{12}$-C$_{24}$-alkyl group. Alternatively, only one of the two radicals may be long-chain (for example having 8 to 40 carbon atoms), and the other may be a methyl, ethyl or propyl group.

Appropriately, the NR$_a$R$_b$ segment is derived from a secondary amine, such as dioctadecylamine, dicocoamine, hydrogenated ditallowamine and methylbehenylamine. Amine mixtures as obtainable from natural materials are likewise suitable. One example is a secondary hydrogenated tallowamine where the alkyl groups are derived from hydrogenated tallow fat, and contain about 4% by weight of C$_{14}$, 31% by weight of C$_{16}$ and 59% by weight of C$_{18}$-alkyl groups. Corresponding tertiary amines of the formula 3 are sold, for example, by Akzo Nobel under the Armeen® M2HT or Armeen® M2C name.

However, the tertiary amine adduct 3 may also be one where the R$_a$, R$_b$ and R$_c$ radicals have identical or different long-chain alkyl radicals, especially straight-chain or branched alkyl groups having 8 to 40 carbon atoms.

Further nonlimiting examples of suitable amines are:

N,N-dimethyl-N-(2-ethylhexyl)amine, N,N-dimethyl-N-(2-propylheptyl)amine, dodecyldimethylamine, hexadecyldimethylamine, oleyldimethylamine, cocoyldimethylamine, dicocoylmethylamine, tallowdimethylamine, ditallowmethylamine, tridodecylamine, trihexadecylamine, trioctadecylamine, soyadimethylamine, tris(2-ethylhexyl)amine, and Alamine 336 (tri-n-octylamine).

A3.2) Quaternizable, Polyether-Substituted Amine Comprising at Least One Quaternizable, Especially Tertiary, Amino Group;

Compounds of this kind are described, for example, in the applicant's WO2013/064689, which is hereby explicitly incorporated by reference.

Substituted amines of this kind especially have at least one, especially one, polyether substituent having monomer units of the general formula Ic $$-[-CH(R_3)-CH(R_4)-O-]-\qquad\text{(Ic)}$$

in which
$R_3$ and $R_4$ are the same or different and are each H, alkyl, alkylaryl or aryl.

The polyether-substituted amine may have a number-average molecular weight in the range from 500 to 5000, especially 800 to 3000 or 900 to 1500.

The quaternizable, polyether-substituted amines are especially nitrogen compounds of the general formula Ia-1 or Ib-2

(Ia-1)

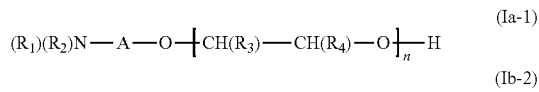
(Ib-2)

in which
$R_1$ and $R_2$ are the same or different and are each alkyl, alkenyl, hydroxyalkyl, hydroxyalkenyl, aminoalkyl or aminoalkenyl, or $R_1$ and $R_2$ together are alkylene, oxyalkylene or aminoalkylene;

$R_3$ and $R_4$ are the same or different and are each H, alkyl, alkylaryl or aryl;

$R_6$ is alkyl, alkenyl, optionally mono- or polyunsaturated cycloalkyl, aryl, in each case optionally substituted, for example by at least one hydroxyl radical or alkyl radical, or interrupted by at least one heteroatom;

A is a straight-chain or branched alkylene radical optionally interrupted by one or more heteroatoms such as N, O and S; and n is an integer value from 1 to 50.

Particular mention should be made of those nitrogen compounds of the formulae Ia-1 and Ib-2 in which $R_1$ and $R_2$ are the same or different and are each $C_1$-$C_6$-alkyl, hydroxy-$C_1$-$C_6$-alkyl, hydroxy-$C_1$-$C_6$-alkenyl, or amino-$C_1$-$C_6$-alkyl, or $R_1$ and $R_2$ together form a $C_2$-$C_6$-alkylene, $C_2$-$C_6$-oxyalkylene or $C_2$-$C_6$-aminoalkylene radical;

$R_3$ and $R_4$ are the same or different and are each H, $C_1$-$C_6$-alkyl or phenyl;

$R_6$ is $C_1$-$C_{20}$-alkyl, for example $C_{10}$-$C_{20}$-, $C_{11}$-$C_{20}$- or $C_{12}$-$C_{20}$-alkyl or aryl or alkylaryl, where alkyl is especially $C_1$-$C_{20}$-;

A is a straight-chain or branched $C_2$-$C_6$-alkylene radical optionally interrupted by one or more heteroatoms such as N, O and S; and n is an integer value from 1 to 30.

Particular mention should additionally be made of reaction products of N,N-dimethylethanolamine and propylene oxide, as described in Synthesis example 1 of WO 2013/064689. This reaction can also be performed without catalysis or with an amine (for example imidazole) as a catalyst, as described, for example, in M. Ionescu, Chemistry and Technology of Polyols for Polyurethanes, 2005, ISBN 978-85957-501-7.

Nitrogen compounds of the general formula Ia-1 are preparable by alkoxylating an aminoalkanol of the general formula II $$(R_1)(R_2)N-A-OH\qquad\text{(II)}$$

in which
$R_1$, $R_2$ and A are each as defined above
with an epoxide of the general formula III

(III)

in which
$R_3$ and $R_4$ are each as defined above
to obtain an alkoxylated amine of the formula

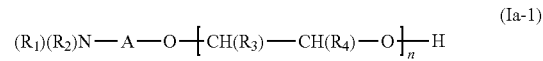
(Ia-1)

in which $R_1$ to $R_4$, A and n are each as defined above.

Nitrogen compounds of the general formula Ia-2 are preparable by alkoxylating an alcohol of the general formula V $$R_6-OH\qquad\text{(V)}$$

in which
$R_6$ is as defined above with an epoxide of the general formula III

(III)

in which
$R_3$ and $R_4$ are each as defined above to obtain a polyether of the formula Ib-1;

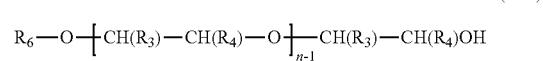
(Ib-1)

in which $R_3$, $R_4$ and $R_6$, A and n are each as defined above and b) then aminating the polyether of the formula Ib-1 thus obtained with an amine of the general formula $$NH(R_1)(R_2)\qquad\text{(VII)}$$

in which $R_1$ and $R_2$ are each as defined above to obtain an amine of the formula Ib-2.

Starting compounds for preparation of polyether-substituted, quaternizable nitrogen compounds are thus:
1) alcohols,
for example of the general formula V $$R_6\text{—OH} \qquad (V)$$

in which $R_6$ is alkyl, alkenyl, optionally mono- or polyunsaturated cycloalkyl, aryl, in each case optionally substituted, for example by at least one hydroxyl radical or alkyl radical, or interrupted by at least one heteroatom;
and
2) amino alkanols,
for example of the general formula II $$(R_1)(R_2)N\text{—A—OH} \qquad (II)$$

in which
$R_1$ and $R_2$ are the same or different and are each alkyl, alkenyl, hydroxyalkyl, hydroxyalkenyl, aminoalkyl or aminoalkenyl, or $R_1$ and $R_2$ together are alkylene, oxyalkylene or aminoalkylene; and
A is a straight-chain or branched alkylene or alkenylene radical optionally interrupted by one or more heteroatoms such as N, O and S.

A further suitable group of quaternizable amino alcohols that should be mentioned is that of compounds selected from hydroxyalkyl-substituted mono- or polyamines having at least one quaternizable, primary, secondary or tertiary amino group and at least one hydroxyl group which can be joined to a polyether radical.

The quaternizable nitrogen compound is especially selected from hydroxyalkyl-substituted primary, secondary and especially tertiary monoamines, and hydroxyalkyl-substituted primary, secondary and especially tertiary diamines.

Examples of suitable "hydroxyalkyl-substituted mono- or polyamines" are those provided with at least one hydroxyalkyl substituted, for example 1, 2, 3, 4, 5 or 6 hydroxyalkyl substituted.

Examples of "hydroxyalkyl-substituted monoamines" include: N-hydroxyalkylmonoamines, N,N-dihydroxyalkylmonoamines and N,N,N-trihydroxyalkylmonoamines, where the hydroxyalkyl groups are the same or different and are also as defined above. Hydroxyalkyl is especially 2-hydroxyethyl, 3-hydroxypropyl or 4-hydroxybutyl.

For example, the following "hydroxyalkyl-substituted polyamines" and especially "hydroxyalkyl-substituted diamines" may be mentioned: N-hydroxyalkylalkylenediamines, N,N-dihydroxyalkylalkylenediamines, where the hydroxyalkyl groups are the same or different and are also as defined above.

Hydroxyalkyl is especially 2-hydroxyethyl, 3-hydroxypropyl or 4-hydroxybutyl; alkylene is especially ethylene, propylene or butylene.

Particular mention should be made of the following quaternizable nitrogen compounds:

| NAME | FORMULA |
|---|---|
| Alcohols with a primary and secondary amine  | |
| ethanolamine | H₂N∼OH |
| 3-hydroxy-1-propylamine | H₂N∼∼OH |
| diethanolamine | HO∼N(H)∼OH |
| diisopropanolamine | HO∼N(H)∼OH (isopropyl) |
| N-(2-hydroxyethyl) ethylenediamine | HO∼N(H)∼NH₂ |
| Alcohols with a tertiary amine  | |
| triethanolamine, (2,2',2''-nitrilotriethanol) | HO∼N(∼OH)∼OH |
| 1-(3-hydroxypropyl)imidazole | HO∼∼N(imidazole) |
| tris(hydroxymethyl)amine | HO∼N(∼OH)∼OH |
| 3-dimethylamino-1-propanol | (CH₃)₂N∼∼OH |
| 3-diethylamino-1-propanol | HO∼∼∼N(Et)₂ |
| 2-dimethylamino-1-ethanol | HO∼N(CH₃)₂ |
| 4-diethylamino-1-butanol | HO∼∼∼∼N(Et)₂ |

For preparation of the polyether-substituted quaternizable compounds (Ia-1 and Ib-1), the procedure may be as follows:

a1) Proceeding from Amino Alcohols of the Formula II:

The amino alcohols of the general formula II can be alkoxylated in a manner known in principle to obtain alkoxylated amines of the general formula Ia-1.

The performance of alkoxylations is known in principle to those skilled in the art. It is likewise known to those skilled in the art that the reaction conditions, especially the selection of the catalyst, can influence the molecular weight distribution of the alkoxylates.

For the alkoxylation, $C_2$-$C_{16}$-alkylene oxides are used, for example ethylene oxide, propylene oxide or butylene oxide. Preference is given to the 1,2-alkylene oxides in each case.

The alkoxylation may be a base-catalyzed alkoxylation. For this purpose, the amino alcohols (II) can be admixed in a pressure reactor with alkali metal hydroxides, preferably potassium hydroxide, or with alkali metal alkoxides, for example sodium methoxide. Water still present in the mixture can be drawn off by means of reduced pressure (for example <100 mbar) and/or increasing the temperature (30 to 150° C.). Thereafter, the alcohol is present in the form of the corresponding alkoxide. This is followed by inertization with inert gas (for example nitrogen) and stepwise addition of the alkylene oxide(s) at temperatures of 60 to 180° C. up to a pressure of max. 10 bar. At the end of the reaction, the catalyst can be neutralized by adding acid (e.g. acetic acid or phosphoric acid) and can be filtered off if required. The basic catalyst can also be neutralized by addition of commercial magnesium silicates, which are subsequently filtered off. Optionally, the alkoxylation can also be performed in the presence of a solvent. This may be, for example, toluene, xylene, dimethylformamide or ethylene carbonate.

The alkoxylation of the amino alcohols can also be undertaken by means of other methods, for example by acid-catalyzed alkoxylation. In addition, it is possible to use, for example, double hydroxide clays, as described in DE 43 25 237 A1, or it is possible to use double metal cyanide catalysts (DMC catalysts). Suitable DMC catalysts are disclosed, for example, in DE 102 43 361 A1, especially paragraphs [0029] to [0041] and the literature cited therein. For example, it is possible to use catalysts of the Zn—Co type. To perform the reaction, the amino alcohol can be admixed with the catalyst, and the mixture dewatered as described above and reacted with the alkylene oxides as described. Typically not more than 1000 ppm of catalyst based on the mixture are used, and the catalyst can remain in the product owing to this small amount. The amount of catalyst may generally be less than 1000 ppm, for example 250 ppm or less.

The alkoxylation can alternatively also be undertaken by reaction of the compounds (IV) and (V) with cyclic carbonates, for example ethylene carbonate.

a2) Proceeding from Alkanols of the Formula V:

As described in the above paragraph a1) for amino alcohols (II), it is analogously also possible to alkoxylate alkanols $R_6OH$ in a manner known in principle to polyethers (Ib-1). The polyethers thus obtained can subsequently be converted to the corresponding polyether amines (Ib-2) by reductive amination with ammonia, primary amines or secondary amines (VII) by customary methods, in continuous or batchwise processes using hydrogenation or amination catalysts customary therefor, for example those comprising catalytically active constituents based on the elements Ni, Co, Cu, Fe, Pd, Pt, Ru, Rh, Re, Al, Si, Ti, Zr, Nb, Mg, Zn, Ag, Au, Os, Ir, Cr, Mo, W or combinations of these elements with one another, in customary amounts. The conversion can be performed without solvent or, in the case of high polyether viscosities, in the presence of a solvent, preferably in the presence of branched aliphatics, for example isododecane. The amine component (VII) is generally used here in excess, for example in a 2- to 100-fold excess, preferably a 10- to 80-fold excess. The reaction is conducted at pressures of 10 to 600 bar over a period of 10 minutes to 10 hours. After cooling, the catalyst is removed by filtering, excess amine component (VII) is evaporated and the water of reaction is distilled off azeotropically or under a gentle nitrogen stream.

Should the resulting polyether amine (Ib-2) have primary or secondary amine functionalities ($R_1$ and/or $R_2$ is H), it can subsequently be converted to a polyether amine having a tertiary amine function ($R_1$ and $R_2$ not H). The alkylation can be effected in a manner known in principle by reaction with alkylating agents. Any alkylating agents are suitable in principle, for example alkyl halides, alkylaryl halides, dialkyl sulfates, alkylene oxides, optionally in combination with acid; aliphatic or aromatic carboxylic esters, such as dialkyl carboxylates in particular; alkanoates; cyclic non-aromatic or aromatic carboxylic esters; dialkyl carbonates; and mixtures thereof. The conversions to the tertiary polyether amine can also take place through reductive amination by reaction with a carbonyl compound, for example formaldehyde, in the presence of a reducing agent. Suitable reducing agents are formic acid or hydrogen in the presence of a suitable heterogeneous or homogeneous hydrogenation catalyst. The reactions can be performed without solvent or in the presence of solvents. Suitable solvents are, for example, $H_2O$, alkanols such as methanol or ethanol, or 2-ethylhexanol, aromatic solvents such as toluene, xylene or solvent mixtures from the Solvesso series, or aliphatic solvents, especially mixtures of branched aliphatic solvents. The reactions are conducted at temperatures of 10° C. to 300° C. at pressures of 1 to 600 bar over a period of 10 minutes to 10 h. The reducing agent is used here at least stoichiometrically, preferably in excess, especially in a 2- to 10-fold excess.

The reaction product thus formed (polyether amine Ib-1 or Ib-2) can theoretically be purified further, or the solvent can be removed. Usually, however, this is not absolutely necessary, and so the reaction product can be transferred without further purification into the next synthesis step, the quaternization.

A3.3) Polyalkene-Substituted Amines Having at Least One Tertiary, Quaternizable Nitrogen Group Further suitable quaternizable nitrogen compounds are polyalkene-substituted amines having at least one tertiary nitrogen group. This group of compounds is likewise known and is described, for example, in WO 2008/060888 or US 2008/0113890 and the further prior art cited therein, which is hereby explicitly incorporated by reference.

Such polyalkene-substituted amines having at least one tertiary amino group are derivable from an olefin polymer and an amine such as ammonia, monoamines, polyamines or mixtures thereof. They can be prepared by a multitude of processes, for example the following processes cited by way of example:

A process for preparing a polyalkene-substituted amine comprises the reaction of a halogenated olefin polymer with an amine, as described in U.S. Pat. Nos. 3,275,554, 3,438,757, 3,454,555, 3,565,804, 3,755,433 and 3,822,289.

A further process for preparing a polyalkene-substituted amine comprises the reaction of a hydroformylated olefin with a polyamine and hydrogenation of the reaction product, as described in U.S. Pat. Nos. 5,567,845 and 5,496,383.

A further process for preparing a polyalkene-substituted amine comprises the conversion of a polyalkene with the aid of a conventional epoxidizing reagent with or without catalyst to the corresponding epoxide and the conversion of the epoxide to the polyalkene-substituted amine by reaction with ammonia or an amine under the conditions of reductive amination, as described in U.S. Pat. No. 5,350,429.

A further process for preparing a polyalkene-substituted amine comprises the hydrogenation of a β-amino nitrile which has been prepared by reaction of an amine with a nitrile, as described in U.S. Pat. No. 5,492,641.

A further process for preparing a polyalkene-substituted amine comprises hydroformylation of a polybutene or polyisobutylene with a catalyst, such as rhodium or cobalt, in the presence of CO and hydrogen at elevated pressures and temperatures, as described in U.S. Pat. No. 4,832,702.

In one embodiment of the invention, the polyalkenes used for the preparation are derived from olefin polymers. The olefin polymers may comprise homopolymers and co-polymers of polymerizable olefin monomers having 2 to about 16 carbon atoms, 2 to about 6 carbon atoms or 2 to about 4 carbon atoms.

Interpolymers are those in which two or more olefin monomers are interpolymerized by known conventional methods, giving polyalkenes having units derived from each of the two or more olefin monomers within their structure.

Thus, "interpolymers" comprise copolymers, terpolymers and tetrapolymers.

"Polyalkenes", from which the polyalkene-substituted amines are derived, are conventionally frequently also referred to as "polyolefins".

The olefin monomers from which the olefin polymers are derived are polymerizable olefin monomers having one or more ethylenically unsaturated groups (i.e. >C=C<); in other words, they are monoolefinic monomers such as ethylene, propylene, 1-butene, isobutene (2-methyl-1-butene), 1-octene, or polyolefinic monomers (usually diolefinic monomers) such as 1,3-butadiene and isoprene.

The olefin monomers are usually polymerizable terminal olefins, i.e. olefins having the >C=CH$_2$ group in their structure. However, it is also possible to use polymerizable internal olefin monomers characterized by groups of the formula >C—C=C—C<.

Specific examples of terminal and internal olefin monomers which can be used to prepare the polyalkenes by conventional methods are: ethylene, propylene, the butenes (butylene), especially 1-butene, 2-butene and isobutylene, 1-pentene, 1-hexene, 1-heptene, 1-octene, 1-nonene, 1-decene, 2-pentene, propylene tetramer, diisobutylene, isobutylene trimer, 1,2-butadiene, 1,3-butadiene, 1,2-pentadiene, 1,3-pentadiene, 1,4-pentadiene, isoprene, 1,5-hexadiene, 2-methyl-5-propyl-1-hexene, 3-pentene, 4-octene and 3,3-dimethyl-1-pentene.

In another embodiment, the olefin polymer is preparable by polymerization of a C$_4$ refinery stream having a butene content of about 35 to about 75 percent by weight and an isobutene content of about 30 to about 60 percent by weight in the presence of a Lewis acid catalyst such as aluminum trichloride or boron trifluoride. These polybutenes typically comprise predominantly (more than about 80% of all the repeat units) repeat isobutene units of the (—CH$_2$—C(CH$_3$)$_2$—) type.

In a further embodiment, the polyalkene substituent of the polyalkene-substituted amine is derived from a polyisobutylene.

In another embodiment, the amines which can be used to form the polyalkene-substituted amine comprise ammonia, monoamines, polyamines or mixtures thereof, including mixtures of various monoamines, mixtures of various polyamines and mixtures of monoamines and polyamines (the diamines). The amines comprise aliphatic, aromatic, heterocyclic and carbocyclic amines. Monoamines and polyamines are characterized by the presence in their structure of at least one HN<group. The amines may be aliphatic, cycloaliphatic, aromatic or heterocyclic.

The monoamines are generally substituted by a hydrocarbyl group having 1 to 50 carbon atoms. These hydrocarbyl groups may especially be aliphatic and free of acetylenically unsaturated groups and have 1 to about 30 carbon atoms. Particular mention should be made of saturated aliphatic hydrocarbyl radicals having 1 to 30 carbon atoms.

In a further embodiment, the monoamines may have the formula HNR$_1$R$_2$ where R$_1$ is a hydrocarbyl group having up to 30 carbon atoms and R$_2$ is hydrogen or a hydrocarbyl group having up to about 30 carbon atoms. Examples of suitable monoamines are methylamine, ethylamine, diethylamine, 2-ethylhexylamine, di(2-ethylhexyl)amine, n-butylamine, di-n-butylamine, allylamine, isobutylamine, cocoamine, stearylamine, laurylamine, methyllaurylamines and oleylamine.

Aromatic monoamines are those monoamines in which a carbon atom in the aromatic ring structure is bonded directly to the amine nitrogen atom. The aromatic ring will usually be a monocyclic aromatic ring (i.e. derived from benzene), but may include fused aromatic rings, especially those derived from naphthalene. Examples of aromatic monoamines are aniline, di(para-methylphenyl)amine, naphthylamine, N-(n-butyl)aniline. Examples of aliphatic-substituted, cycloaliphatic-substituted and heterocyclic-substituted aromatic monoamines are: para-dodecylaniline, cyclohexyl-substituted naphthylamine and thienyl-substituted aniline.

Hydroxylamines are likewise suitable monoamines. Compounds of this kind are the hydroxyhydrocarbyl-substituted analogs of the aforementioned monoamines.

In one embodiment, the hydroxy monoamines of the formula HNR$_3$R$_4$ where R$_3$ is a hydroxyl-substituted alkyl group having up to about 30 carbon atoms, and in one embodiment up to about 10 carbon atoms; and R$_4$ is a hydroxyl-substituted alkyl group having up to about 30 carbon atoms, hydrogen or a hydrocarbyl group having up to about 10 carbon atoms. Examples of hydroxyl-substituted monoamines include: ethanolamine, di-3-propanolamine, 4-hydroxybutylamine, diethanolamine and N-methyl-2-hydroxypropylamine.

In another embodiment, the amine of the polyalkene-substituted amines may be a polyamine. The polyamine may be aliphatic, cycloaliphatic, heterocyclic or aromatic. Examples of the polyamines include: alkylenepolyamines, hydroxyl group-comprising polyamines, aryl polyamines and heterocyclic polyamines.

The alkylenepolyamines comprise those of the following formula:

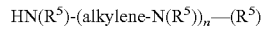

HN(R$^5$)-(alkylene-N(R$^5$))$_n$—(R$^5$)

in which n is in the range from 1 to about 10 and, for example, in the range from 2 to about 7, or from 2 to about 5, and the "alkylene" group has 1 to about 10 carbon atoms, for example 2 to about 6, or 2 to about 4 carbon atoms;

the R$^5$ radicals are each independently hydrogen, an aliphatic group, a hydroxyl- or amine-substituted aliphatic group of up to about 30 carbon atoms in each case. Typically, R$^5$ is H or lower alkyl (an alkyl group having 1 to about 5 carbon atoms), especially H. Alkylenepolyamines of this kind include: methylenepolyamines, ethylenepolyamines, butylenepolyamines, propylenepolyamines, pentylenepolyamines, hexylenepolyamines and heptylenepolyamines. The higher homologs of such amines and related aminoalkyl-substituted piperazines are likewise included.

Specific alkylenepolyamines for preparation of the polyalkene-substituted amines are the following: ethylenediamine, diethylenetriamine, triethylenetetramine, tetraethylenepentamine, propylenediamine, 3-dimethylaminopropylamine, trimethylenediamine, hexamethylenediamine, decamethylenediamine, octamethylenediamine, di(heptamethylene)triamine, tripropylenetetramine, pentaethylenehexamine, di(trimethylenetriamine), N-(2-aminoethyl)piperazine and 1,4-bis(2-aminoethyl)piperazine.

Ethylenepolyamines, such as those mentioned above, are particularly suitable for reasons of cost and effectiveness. Polyamines of this kind are described in detail in the chapter "Diamine und höhere Amine" [Diamines and Higher Amines] in Encyclopedia of Chemical Technology, second edition, Kirk-Othmer, volume 7, pages 27-39, Inter-science Publishers, division of John Wiley & Sons, 1965. Compounds of this kind are most conveniently prepared by the reaction of an alkylene chloride with ammonia or by reaction of an ethyleneimine with a ring-opening reagent such as ammonia. These reactions lead to preparation of complex mixtures of alkylenepolyamines, including cyclic condensation products such as piperazines.

Other suitable types of polyamine mixtures are the products which are formed as residue by stripping the above-described polyamine mixtures and are frequently referred to as "polyamine bottoms". In general, alkylenepolyamine bottom products those which comprise less than two, usually less than 1%, by weight of material that boils below about 200° C. A typical example of such ethylenepolyamine bottoms is that of the products designated "E 100" from Dow Chemical Company in Freeport, Tex. These alkylenepolyamine bottoms comprise cyclic condensation products such as piperazine and higher analogs of diethylenetriamine, triethylenetetramines and the like.

Hydroxyl group-comprising polyamines include: hydroxyalkylalkylenepolyamines having one or more hydroxyalkyl substituents on the nitrogen atoms. Polyamines of this kind can be prepared by reacting the above-described alkylenepolyamines with one or more alkylene oxides (e.g. ethylene oxide, propylene oxide and butylene oxide). Similar alkylene oxide-alkanolamine reaction products may also, for example, be the products of the reaction of primary, secondary or tertiary alkanolamines with ethylene, propylene or higher epoxides in a molar ratio of 1:1 to 1:2. Reactant ratios and temperatures for performance of such reactions are known to those skilled in the art.

In another embodiment, the hydroxyalkyl-substituted alkylenepolyamine may be a compound in which the hydroxyalkyl group is a hydroxy-lower alkyl group, i.e. has fewer than eight carbon atoms. Examples of such hydroxyalkyl-substituted polyamines include N-(2-hydroxyethyl)ethylenediamine (also known as 2-(2-aminoethylamino)ethanol), N, N-bis(2-hydroxyethyl)ethylenediamine, 1-(2-hydroxyethyl)piperazine, monohydroxypropyl-substituted diethylenetriamine, dihydroxypropyl-substituted tetraethylenepentamine and N-(3-hydroxybutyl)tetramethylenediamine.

Aryl polyamines are analogs of the abovementioned aromatic monoamines. Examples of aryl polyamines include: N,N'-di-n-butyl-para-phenylenediamine and bis(para-aminophenyl)methane.

Heterocyclic mono- and polyamines may comprise: aziridines, azetidines, azolidines, pyridines, pyrroles, indoles, piperidines, imidazoles, piperazines, isoindoles, purines, morpholines, thiomorpholines, N-aminoalkylmorpholines, N-aminoalkylthiomorpholines, N-aminoalkylpiperazines, N,N'-diaminoalkylpiperazines, azepines, azocines, azonines, azecines and tetra-, di- and perhydro derivatives of each of the above compounds and mixtures of two or more of these heterocyclic amines. Typical heterocyclic amines are saturated 5- and 6-membered heterocyclic amines having only nitrogen, oxygen and/or sulfur in the heterocycle, especially piperidines, piperazines, thiomorpholines, morpholines, pyrrolidines and the like. Piperidine, aminoalkyl-substituted piperidines, piperazine, aminoalkyl-substituted piperazines, morpholine, aminoalkyl-substituted morpholines, pyrrolidine and aminoalkyl-substituted pyrrolidines are particularly preferred. Usually, the aminoalkyl substituents are bonded to a nitrogen atom which is part of the heterocycle.

Specific examples of such heterocyclic amines include N-aminopropylmorpholine, N-aminoethylpiperazine and N,N'-diaminoethylpiperazine. Hydroxyheterocyclic polyamines are also suitable. Examples include: N-(2-hydroxyethyl)cyclohexylamine, 3-hydroxycyclopentylamine, para-hydroxyaniline and N-hydroxyethylpiperazine.

Examples of polyalkene-substituted amines are as follows: poly(propylene)amine, poly(butene)amine, N,N-dimethylpolyisobutyleneamines; polybutenemorpholines, N,N-poly(butene)ethylenediamine, N-poly(propylene)trimethylenediamine, N-poly(butene), diethylenetriamine, N',N'-poly(butene)tetraethylenepentamine and N,N-dimethyl-N'-poly(propylene)-1,3-propylenediamine.

The number-average molecular weight of such polyalkene-substituted amines is about 500 to about 5000, for example 1000 to about 1500 or about 500 to about 3000.

Any of the abovementioned polyalkene-substituted amines which are secondary or primary amines can be alkylated to tertiary amines with alkylating agents which are also known as quaternizing agents, such as dialkyl sulfates, alkyl halides, hydrocarbyl-substituted carbonates; hydrocarbyl epoxides in combination with an acid and mixtures thereof. If particular quaternizing agents, such as alkyl halides or dialkyl sulfates, are used, it may be necessary to provide a base or basic compositions, such as sodium carbonate or sodium hydroxide, to give the free tertiary amine form. Primary amines require two equivalents of alkylating agent and two equivalents of base to obtain a tertiary amine. In another embodiment, the alkylation of primary amines can frequently be conducted in four successive steps, first a treatment with the alkylating agent and second treatment with a base and then repetition of the two steps. In another embodiment, the alkylation of a primary amine will be effected in one step, for example using two moles of alkyl halide in the presence of an excess of heterogeneous base, such as sodium carbonate. The polyamine can be exhaustively or partially alkylated in a manner known per se.

In another embodiment, the alkylation of primary amines and secondary amines to tertiary amines can be effected with epoxides. Unlike the use of the alkyl halides, no treatment with base is required in the case of use of an epoxide to obtain the free amine. Typically, in the case of alkylation of amines with epoxides, at least one mole of epoxide is used for each hydrogen atom in the amine. In the alkylation to give the tertiary amine with an epoxide, neither additional acid nor base is required.

Particular preference is additionally given to polyisobutenedimethylamine obtainable by hydroformylating polyisobutene (Mn 1000) and subsequent reductive amination with dimethylamine; see Example B of WO 2008/060888.

A3.4) Reaction Products of a Hydrocarbyl-Substituted Acylating Agent and a Compound Comprising a Nitrogen or Oxygen Atom and Additionally Comprising at Least One Quaternizable Amino Group Compounds of this kind are described, for example, in the applicant's WO2013/000997, which is hereby explicitly incorporated by reference.

Suitable hydrocarbyl-substituted polycarboxylic acid compounds, or hydrocarbyl-substituted acylating agents, include:

The polycarboxylic acid compounds used are aliphatic di- or polybasic (for example tri- or tetrabasic), especially from di-, tri- or tetracarboxylic acids and analogs thereof, such as anhydrides or lower alkyl esters (partially or completely esterified), and is optionally substituted by one or more (for example 2 or 3), especially a long-chain alkyl radical and/or a high molecular weight hydrocarbyl radical, especially a polyalkylene radical. Examples are $C_3$-$C_{10}$ polycarboxylic acids, such as the dicarboxylic acids malonic acid, succinic acid, glutaric acid, adipic acid, pimelic acid, suberic acid, azelaic acid and sebacic acid, and the branched analogs thereof; and the tricarboxylic acid citric acid; and anhydrides or lower alkyl esters thereof of. The polycarboxylic acid compounds can also be obtained from the corresponding monounsaturated acids and addition of at least one long-chain alkyl radical and/or high molecular weight hydrocarbyl radical. Examples of suitable monounsaturated acids are fumaric acid, maleic acid, itaconic acid.

The hydrophobic "long-chain" or "high molecular weight" hydrocarbyl radical which ensures sufficient solubility of the quaternized product in the fuel has a number-average molecular weight ($M_n$) of 85 to 20000, for example 113 to 10000, or 200 to 10 000 or 350 to 5000, for example 350 to 3000, 500 to 2500, 700 to 2500, or 800 to 1500. Typical hydrophobic hydrocarbyl radicals include polypropenyl, polybutenyl and polyisobutenyl radicals, for example with a number-average molecular weight $M_n$ of 3500 to 5000, 350 to 3000, 500 to 2500, 700 to 2500 and 800 to 1500.

Suitable hydrocarbyl-substituted compounds are described, for example, in DE 43 19 672 and WO 2008/138836.

Suitable hydrocarbyl-substituted polycarboxylic acid compounds also comprise polymeric, especially dimeric, forms of such hydrocarbyl-substituted polycarboxylic acid compounds. Dimeric forms comprise, for example, two acid anhydride groups which can be reacted independently with the quaternizable nitrogen compound in the preparation process according to the invention.

The quaternizable nitrogen compounds reactive with the above polycarboxylic acid compound are selected from
a. hydroxyalkyl-substituted mono- or polyamines having at least one quaternized (e.g. choline) or quaternizable primary, secondary or tertiary amino group;
b. straight-chain or branched, cyclic, heterocyclic, aromatic or nonaromatic polyamines having at least one primary or secondary (anhydride-reactive) amino group and having at least one quaternized or quaternizable primary, secondary or tertiary amino group;
c. piperazines.

The quaternizable nitrogen compounds are especially selected from
d. hydroxyalkyl-substituted primary, secondary, tertiary or quaternary monoamines and hydroxyalkyl-substituted primary, secondary, tertiary or quaternary diamines;
e. straight-chain or branched aliphatic diamines having two primary amino groups; di- or polyamines having at least one primary and at least one secondary amino group; di- or polyamines having at least one primary and at least one tertiary amino group; di- or polyamines having at least one primary and at least one quaternary amino group; aromatic carbocyclic diamines having two primary amino groups; aromatic heterocyclic polyamines having two primary amino groups; aromatic or nonaromatic heterocycles having one primary and one tertiary amino group.

Examples of suitable "hydroxyalkyl-substituted mono- or polyamines" are those provided with at least one hydroxyalkyl substituted, for example 1, 2, 3, 4, 5 or 6 hydroxyalkyl substituted.

Examples of "hydroxyalkyl-substituted monoamines" include: N-hydroxyalkylmonoamines, N,N-dihydroxyalkylmonoamines and N,N,N-trihydroxyalkylmonoamines, where the hydroxyalkyl groups are the same or different and are also as defined above. Hydroxyalkyl is especially 2-hydroxyethyl, 3-hydroxypropyl or 4-hydroxybutyl.

For example, the following "hydroxyalkyl-substituted polyamines" and especially "hydroxyalkyl-substituted diamines" may be mentioned: N-hydroxyalkylalkylenediamines, N, N-dihydroxyalkylalkylenediamines, where the hydroxyalkyl groups are the same or different and are also as defined above. Hydroxyalkyl is especially 2-hydroxyethyl, 3-hydroxypropyl or 4-hydroxybutyl; alkylene is especially ethylene, propylene or butylene.

Suitable "diamines" are alkylenediamines, and the N-alkyl-substituted analogs thereof, such as N-monoalkylated alkylenediamines and the N,N- or N,N'-dialkylated alkylenediamines. Alkylene is especially straight-chain or branched $C_{1-7}$- or $C_{1-4}$-alkylene as defined above. Alkyl is especially $C_{1-4}$-alkyl as defined above. Examples are especially ethylenediamine, 1,2-propylenediamine, 1,3-propylenediamine, 1,4-butylenediamine and isomers thereof, pentanediamine and isomers thereof, hexanediamine and isomers thereof, heptanediamine and isomers thereof, and singly or multiply, for example singly or doubly, $C_1$-$C_4$-alkylated, for example methylated, derivatives of the aforementioned diamine compounds such as 3-dimethylamino-1-propylamine (DMAPA), N,N-diethylaminopropylamine and N,N-dimethylaminoethylamine.

Suitable straight-chain "polyamines" are, for example, dialkylenetriamine, trialkylenetetramine, tetraalkylenepentamine, pentaalkylenehexamine, and the N-alkyl-substituted analogs thereof, such as N-monoalkylated and the N,N- or N,N'-dialkylated alkylenepolyamines. Alkylene is especially straight-chain or branched $C_{1-7}$- or $C_{1-4}$-alkylene as defined above. Alkyl is especially $C_{1-4}$-alkyl as defined above.

Examples are especially diethylenetriamine, triethylenetetramine, tetraethylenepentamine, pentaethylenehexamine, dipropylenetriamine, tripropylenetetramine, tetrapropylenepentamine, pentapropylenehexamine, dibutylenetriamine, tributylenetetramine, tetrabutylenepentamine, pentabutylenehexamine; and the N,N-dialkyl derivatives thereof, especially the N,N-di-$C_{1-4}$-alkyl derivatives thereof. Examples include: N,N-dimethyldimethylenetriamine, N,N-diethyldimethylenetriamine, N,N-dipropyldimethylenetriamine, N,N-dimethyldiethylene-1,2-triamine, N, N-diethyldiethylene-1,2-triamine, N,N-dipropyldiethylene-1,2-triamine, N,N-dimethyldipropylene-1,3-triamine (i.e. DMAPAPA), N,N-diethyldipropylene-1,3-triamine, N, N-dipropyldipropylene-1,3-triamine, N,N-dimethyldibutylene-1,4-triamine, N,N-diethyldibutylene-1,4-triamine, N,N-dipropyldibutylene-1,4-triamine, N,N-dimethyldipentylene-1,5-triamine, N,N-diethyldipentylene-1,5-triamine, N,N-dipropyldipentylene-1,5-triamine, N,N- dimethyldihexylene-1,6-triamine, N, N-diethyldihexylene-1,6-triamine and N,N-dipropyldihexylene-1,6-triamine.

"Aromatic carbocyclic diamines" having two primary amino groups are the diamino-substituted derivatives of benzene, biphenyl, naphthalene, tetrahydronaphthalene, fluorene, indene and phenanthrene.

"Aromatic or nonaromatic heterocyclic polyamines" having two primary amino groups are the derivatives, substituted by two amino groups, of the following heterocycles:
- 5- or 6-membered, saturated or monounsaturated heterocycles comprising one to two nitrogen atoms and/or one oxygen or sulfur atom or one or two oxygen and/or sulfur atoms as ring members, for example tetrahydrofuran, pyrrolidine, isoxazolidine, isothiazolidine, pyrazolidine, oxazolidine, thiazolidine, imidazolidine, pyrroline, piperidine, piperidinyl, 1,3-dioxane, tetrahydropyran, hexahydropyridazine, hexahydropyrimidine, piperazine;
- 5-membered aromatic heterocycles comprising, in addition to carbon atoms, one, two or three nitrogen atoms or one or two nitrogen atoms and one sulfur or oxygen atom as ring members, for example furan, thiane, pyrrole, pyrazole, oxazole, thiazole, imidazole and 1,3,4-triazole; isoxazole, isothiazole, thiadiazole, oxadiazole;
- 6-membered heterocycles comprising, in addition to carbon atoms, one or two, or one, two or three, nitrogen atoms as ring members, for example pyridinyl, pyridazine, pyrimidine, pyrazinyl, 1,2,4-triazine, 1,3,5-triazin-2-yl.

"Aromatic or nonaromatic heterocycles having one primary and one tertiary amino group" are, for example, the abovementioned N-heterocycles which are aminoalkylated on at least one ring nitrogen atom, and especially bear an amino-$C_{1-4}$-alkyl group.

"Aromatic or nonaromatic heterocycles having one tertiary amino group and one hydroxyalkyl group" are, for example, the abovementioned N-heterocycles which are hydroxyalkylated on at least one ring nitrogen atom, and especially bear a hydroxy-$C_{1-4}$-alkyl group.

Particular mention should be made especially of the following groups of individual classes of quaternizable nitrogen compounds:

Group 1:

| NAME | FORMULA |
|---|---|
| Diamines with primary second nitrogen atom | |
| ethylenediamine | $H_2N$—$CH_2CH_2$—$NH_2$ |
| 1,2-propylenediamine | $H_2N$—$CH(CH_3)CH_2$—$NH_2$ |
| 1,3-propylenediamine | $H_2N$—$(CH_2)_3$—$NH_2$ |
| Isomeric butylenediamines, for example | $H_2N$—$CH_2CH(CH_3)CH_2$—$NH_2$ |
| 1,5-pentylenediamine | $H_2N$—$(CH_2)_5$—$NH_2$ |
| Isomeric pentanediamines, for example | $H_2N$—$CH_2CH_2CH(CH_3)CH_2$—$NH_2$ |
| Isomeric hexanediamines, for example | $H_2N$—$CH_2CH_2CH(C_2H_5)CH_2$—$NH_2$ |
| Isomeric heptanediamines, for example | $H_2N$—$CH_2CH_2CH(C_2H_5)CH(CH_3)$—$NH_2$ |
| Di- and polyamines with a secondary second nitrogen atom | |
| diethylenetriamine (DETA) | $H_2N$—$CH_2CH_2$—$NH$—$CH_2CH_2$—$NH_2$ |
| dipropylenetriamine (DPTA), 3,3'-iminobis(N,N-dimethylpropylamine) | $H_2N$—$(CH_2)_3$—$NH$—$(CH_2)_3$—$NH_2$ |
| triethylenetetramine (TETA) | $H_2N$—$CH_2CH_2$—$NH$—$CH_2CH_2$—$NH$—$CH_2CH_2$—$NH_2$ |
| tetraethylenepentamine (TEPA) | branched structure with multiple NH groups |
| pentaethylenehexamine | branched structure with multiple NH groups |
| N-methyl-3-amino-1-propylamine | $CH_3$—$NH$—$(CH_2)_3$—$NH_2$ |
| bishexamethylene-triamine | $H_2N$—$(CH_2)_6$—$NH$—$(CH_2)_6$—$NH_2$ with additional $NH_2$ branch |
| Aromatics | |
| Diaminobenzenes, for example | 1,2-diaminobenzene structure |
| Diaminopyridines, for example | 2,3-diaminopyridine structure |

| NAME | FORMULA |
|---|---|
| Heterocycles | |
| 1-(3-aminopropyl)imidazole | 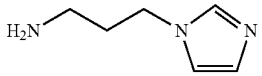 |
| 4-(3-aminopropyl)morpholine | 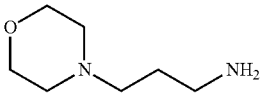 |
| 1-(2-aminoethylpiperidine) | 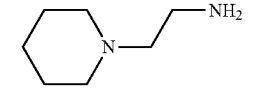 |
| 2-(1-piperazinyl)ethylamine (AEP) | 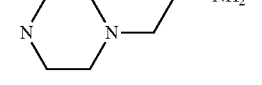 |
| N-methylpiperazine | 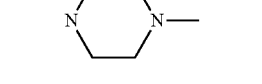 |
| Amines with a tertiary second nitrogen atom | |
| 3,3-diamino-N-methyldipropylamine | 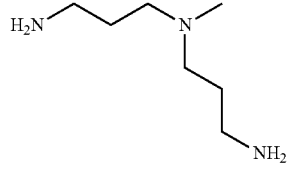 |
| 3-dimethylamino-1-propylamine (DMAPA) | 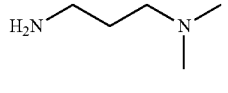 |
| N,N-diethylaminopropylamine | 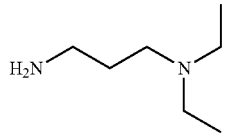 |
| N,N-dimethylaminoethylamine |  |

Group 3:

| NAME | FORMULA |
|---|---|
| Alcohols with a primary and secondary amine | |
| ethanolamine | 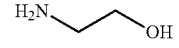 |
| 3-hydroxy-1-propylamine | 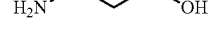 |
| diethanolamine | 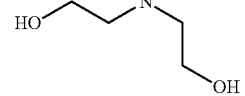 |

-continued

| NAME | FORMULA |
|---|---|
| diisopropanolamine | 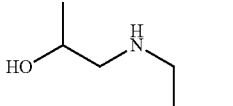 |
| N-(2-hydroxyethyl)ethylenediamine | 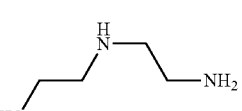 |
| Alcohols with a tertiary amine | |
| triethanolamine, (2,2',2''-nitrilotriethanol) | 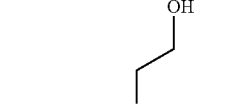 |
| 1-(3-hydroxypropyl)imidazole | 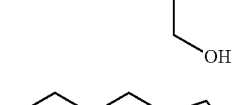 |
| tris(hydroxymethyl)amine | 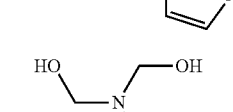 |
| 3-dimethylamino-1-propanol | 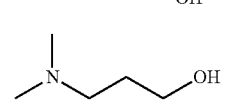 |
| 3-diethylamino-1-propanol | 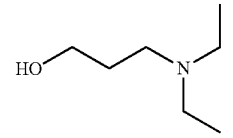 |
| 2-dimethylamino-1-ethanol | 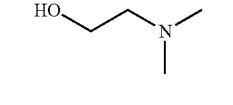 |
| 4-diethylamino-1-butanol | 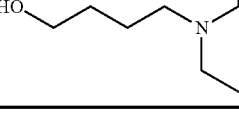 |

The hydrocarbyl-substituted polycarboxylic acid compound can be reacted with the quaternizable nitrogen compound under thermally controlled conditions, such that there is essentially no condensation reaction. More particularly, no formation of water of reaction is observed in that case. More particularly, such a reaction is effected at a temperature in the range from 10 to 80° C., especially 20 to 60° C. or 30 to 50° C. The reaction time may be in the range from a few minutes or a few hours, for example about 1 minute up to about 10 hours. The reaction can be effected at pressure at about 0.1 to 2 atm, but especially at about standard pressure. For example, an inert gas atmosphere is appropriate, for example nitrogen.

More particularly, the reaction can also be effected at elevated temperatures which promote condensation, for example in the range from 90 to 100° C. or 100 to 170° C. The reaction time may be in the region of a few minutes or a few hours, for example about 1 minute up to about 10 hours. The reaction can be effected at pressure at about 0.1 to 2 atm, but especially at about standard pressure.

The reactants are initially charged especially in about equimolar amounts; optionally, a small molar excess of the polycarboxylic acid compound, for example a 0.05- to 0.5-fold, for example a 0.1- to 0.3-fold, excess, is desirable. If required, the reactants can be initially charged in a suitable inert organic aliphatic or aromatic solvent or a mixture thereof. Typical examples are, for example, solvents of the Solvesso series, toluene or xylene. The solvent can also serve, for example, to remove water of condensation azeotropically from the reaction mixture. More particularly, however, the reactions are performed without solvent.

The reaction product thus formed can theoretically be purified further, or the solvent can be removed. Usually, however, this is not absolutely necessary, such that the reaction product can be transferred without further purification into the next synthesis step, the quaternization.

Particular mention should be made of the condensation product of polyisobutylenesuccinic anhydride (Glissopal® SA from BASF, prepared from polyisobutene (Mn 1000) and maleic anhydride in a known manner) and N,N-dimethyl-1,3-diaminopropane (CAS 109-55-7), see Preparation example 1 of WO 2013/000997.

A4) Quaternizing Agents

Useful quaternizing agents in principle include all polycarboxylic esters (partly or fully esterified) suitable as such. Particular mention should be made of partly or especially fully esterified aliphatic or aromatic polycarboxylic esters, such as especially dialkyl carboxylates; cyclic nonaromatic or aromatic polycarboxylic esters and especially the lower alkyl esters thereof, i.e. particularly the $C_{1-4}$- or $C_{1-3}$-alkyl esters.

Examples are especially compounds of the above general formula 2

$$R_1OC(O)\text{-}A\text{-}C(O)OR_{1a} \qquad (2)$$

in which $R_1$, $R_{1a}$ and A are each as defined above.

Suitable examples are alkyl esters derived from carboxylic acids of the above formula 2, the $pK_a$ of which is less than 3.5.

Further examples are especially compounds of the above formula 2, specifically fully esterified alkyl esters, especially the $C_{1-4}$- or $C_{1-3}$-alkyl, more particularly methyl or ethyl, esters, derived from saturated unsubstituted dicarboxylic acids, such as oxalic acid, malonic acid, succinic acid, glutaric acid, adipic acid, pimelic acid and suberic acid;

saturated substituted dicarboxylic acids such as alkyl- or alkenylsuccinic acids, 2-methylbutanedioic acid, 2-ethylpentanedioic acid, 2-n-dodecylbutanedioic acid, 2-n-dodecenylbutanedioic acid, 2-phenylbutanedioic acid and 2-(p-methylphenyl)butanedioic acid; polysubstituted alkyldicarboxylic acids such as 2,2-dimethylbutanedioic acid; 2,3-dimethylbutanedioic acid; 2,3,4-trimethylpentanedioic acid; 2,2,3-trimethylpentanedioic acid and 2-ethyl-3-methylbutanedioic acid;

unsaturated dicarboxylic acids, such as maleic acid, fumaric acid, pent-2-enedioic acid, hex-2-enedioic acid, hex-3-enedioic acid, 5-methylhex-2-enedioic acid, 2,3-dimethylpent-2-enedioic acid, 2-methylbut-2-enedioic acid, 2-dodecylbut-2-enedioic acid and 2-polyisobutylbut-2-enedioic acid;

aromatic dicarboxylic acids, such as phthalic acid, isophthalic acid, terephthalic acid and substituted phthalic acids or 3-methylbenzene-1,2-dicarboxylic acid; 4-phenylbenzene-1,3-dicarboxylic acid; 2-(1-propenyl)benzene-1,4-dicarboxylic acid and 3,4-dimethylbenzene-1,2-dicarboxylic acid; and aromatic or nonaromatic polycarboxylic acids, such as citric acid, 1,2,4-benzenetricarboxylate, 1,2,4,5-benzenetetracarboxylate.

Particular mention should be made of the fully esterified lower alkyl esters, i.e. particularly of the $C_{1-4}$- or $C_{1-3}$-alkyl, more particularly methyl or ethyl, esters, of oxalic acid, phthalic acid, maleic acid, malonic acid and citric acid.

In a particular embodiment, however, the at least one quaternizable tertiary nitrogen atom is quaternized with at least one quaternizing agent selected from compounds of the general formula 2

$$R_1OC(O)\text{-}A\text{-}C(O)OR_{1a} \qquad (2)$$

in which $R_1$ and $R_{1a}$ are each independently a lower alkyl radical, particularly $C_{1-4}$- or $C_{1-3}$-alkyl, especially methyl or ethyl, and A is a chemical bond or optionally mono- or polysubstituted hydrocarbylene (such as, more particularly, an optionally mono- or polysubstituted $C_1$-$C_7$-alkylene or $C_2$-$C_7$-alkenylene); where suitable substituents are, for example, selected from OH, $NH_2$, $NO_2$, or $C(O)OR_3$, especially OH and $C(O)OR_3$, where $R_3$ is H or especially lower alkyl.

Abovementioned esters are typically used in the presence of acids, especially in the presence of free protic acids such as, in particular, with $C_{1-12}$-monocarboxylic acids such as formic acid, acetic acid or propionic acid, or $C_{2-12}$-dicarboxylic acids such as oxalic acid or adipic acid; or else in the presence of sulfonic acids such as benzenesulfonic acid or toluenesulfonic acid, or aqueous mineral acids such as sulfuric acid or hydrochloric acid.

A5) Alcohols and Amines for Transesterification or Amidation

For the inventive derivatization step b) (i.e. transesterification or amidation of the free acid/ester group of the quaternized compounds), alcohols or amines known per se are suitable. The inventive transesterification or amidation converts especially short-chain hydrocarbyl ester groups such as, more particularly, $C_{1-4}$ or $C_{1-3}$ alkyl ester groups, to longer-chain homologs, for example longer-chain alkyl ester or longer-chain alkylamido groups.

a) Transesterification:

According to the following reaction scheme:

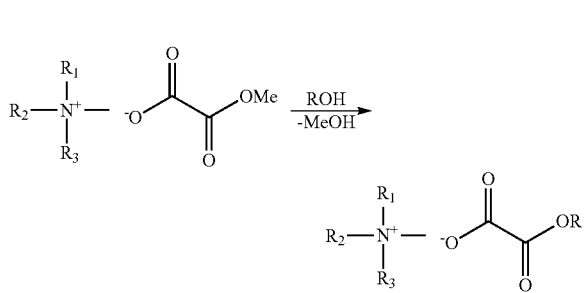

For the transesterification, for example, especially the following alcohols of the formula ROH in which R is a hydrocarbyl radical, especially a long-chain hydrocarbyl radical, are suitable. Examples are:

saturated or unsaturated linear, branched or cyclic aliphatic $C_4$-$C_{30}$ or $C_5$-$C_{28}$, $C_6$-$C_{26}$, $C_7$-$C_{24}$ or $C_8$-$C_{24}$ mono- or polyols and derivatives (especially partly esterified polyols having at least one free hydroxyl group) thereof, such as, more particularly, butanol (all isomers), pentanol (all isomers), hexanol (all isomers), heptanol (all isomers), octanol (all isomers, especially 2-ethylhexanol), nonanol (all isomers), decanol (all isomers, especially 2-propylheptanol), undecanol (all isomers), dodecanol (all isomers), tridecanol (all isomers), tetradecanol (all isomers), pentadecanol (all isomers), hexadecanol (all isomers), octadecanol (all isomers), behenyl alcohol, 1,6-hexanediol, neopentyl glycol, trimethylolpropane, pentaerythritol, glycerol, glyceryl fatty acid esters such as glyceryl monooleate, diglycerol, triglycerol, polyglycerol, partly esterified diglycerols, partly esterified triglycerols, partly esterified polyglycerols. Oleyl alcohols (sold by BASF under the Ocenol® trade name) having iodine numbers of 20-150 (to DGF C-V 11 b).

polyalkoxylates, especially as homopolymers or copolymers (random or block) of the general structural formula 1

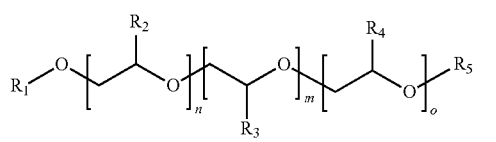

(1)

in which:

$R_1$ and $R_5$ are each independently H, alkyl, alkenyl or aryl, where at least one of the two radicals is H, $R_2$, $R_3$ and $R_4$ are each independently H, $C_1$-$C_{30}$-alkyl, especially $C_1$-$C_5$ alkyl such as methyl or ethyl;

n, m, o are each independently integer values from 0 to 100;

having molecular masses in the range from 40 to 10 000 g/mol, found by determining the OH number (DIN 53240-2); see also M. Ionescu, Chemistry and Technology of Polyols for Polyurethanes, 2005, ISBN 978-1-85957-501-7, Chapter 3, such as, more particularly, carrier oils as described, for example, in section B) below.

Polyol-started polyalkoxylate, especially using ethylene oxide or propylene oxide or butylene oxide (homopolymers or copolymers (random or block)) having molecular masses in the range from 100 to 10 000 g/mol, found by determining the OH number (DIN 53240-2); see also M. Ionescu, Chemistry and Technology of Polyols for Polyurethanes, 2005, ISBN 978-1-85957-501-7, Chapter 3.

Polyethers obtained by polymerizing tetrahydrofuran (polyTHF® from BASF) having molecular weights of 200 to 3000, found by determining the OH number (method STI 8444).

Polyisobutylene alcohol, obtainable by hydroformylation and reduction of polyisobutene having molecular masses of 150 to 5000, found by gel permeation chromatography (THF solvent, polystyrene standard).

b) Amidation
According to the following reaction scheme:

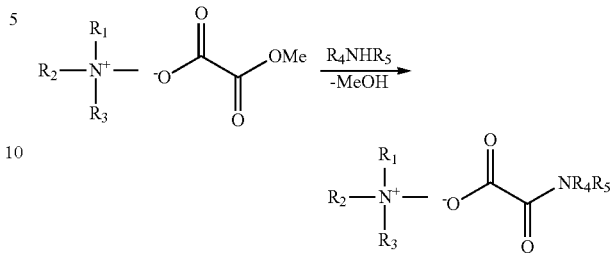

For the amidation, amines of the formula $R_4NHR_5$ where both of the $R_4$ and $R_5$ radicals are hydrocarbyl and at least one of the $R_4$ and $R_5$ radicals is a long-chain hydrocarbyl radical.

For example, especially the following amines are suitable:
saturated or unsaturated linear, branched or cyclic aliphatic primary or secondary aliphatic $C_4$-$C_{30}$, $C_5$-$C_{28}$, $C_6$-$C_{26}$, $C_7$-$C_{24}$ or $C_8$-$C_{24}$ mono- or polyamines, especially butylamine (all isomers), pentylamine (all isomers), hexylamine (all isomers), 2-propylheptylamine, octylamine (all isomers, especially 2-ethylhexylamine), dodecylamine, cocoylamine ($C_{12/14}$—$NH_2$), oleylamine, stearylamine ($C_{16/18}$—$NH_2$), tridecylamine;
polyisobutyleneamines (for example Kerocom PIBA® from BASF)

A6) Preparation of Inventive Additives a) Quaternization
The quaternization is performed in a manner known per se.

To perform the quaternization, the tertiary amine is admixed with at least one compound of the above formula 2, especially in the stoichiometric amounts required to achieve the desired quaternization. It is possible to use, for example, 0.1 to 5.0, 0.2 to 3.0 or 0.5 to 2.5 equivalents of quaternizing agent per equivalent of quaternizable tertiary nitrogen atom. More particularly, however, about 1 to 2 equivalents of quaternizing agent are used in relation to the tertiary amine, in order to fully quaternize the tertiary amine group.

Typical working temperatures here are in the range from 50 to 180° C., for example 90 to 160° C. or 100 to 140° C. The reaction time may be in the region of a few minutes or a few hours, for example about 10 minutes up to about 24 hours. The reaction can be effected at a pressure of about 0.1 to 20 bar, for example 1 to 10 or 1.5 to 3 bar, but especially at about standard pressure.

If required, the reactants can be initially charged for the quaternization in a suitable inert organic aliphatic or aromatic solvent or a mixture thereof. Typical examples are, for example, solvents of the Solvesso series, toluene or xylene, or ethylhexanol. However, the quaternization can also be performed in the absence of a solvent.

To perform the quaternization, the addition of catalytically active amounts of an acid may be appropriate. Preference is given to aliphatic monocarboxylic acids, for example $C_1$-$C_{18}$-monocarboxylic acids such as, more particularly, lauric acid, isononanoic acid or 3,5,5-trimethylhexanoic acid or neodecanoic acid, but also aliphatic dicarboxylic acids or polybasic aliphatic carboxylic acids with a carbon atom number in the range specified above. The quaternization can also be performed in the presence of a Lewis acid. The quaternization can, however, also be performed in the absence of any acid.

b) Transesterification

Suitable conditions are common knowledge and are described, for example in standard organic chemistry textbooks, for example Vollhardt, Organic Chemistry, Wiley publishers, Morrison Boyd, Organic Chemistry, VCh, Otera, Esterification, Wiley publishers.

c) Amidation

Suitable conditions are common knowledge and are described, for example in standard organic chemistry textbooks, for example Vollhardt, Organic Chemistry, Wiley publishers, Morrison Boyd, Organic Chemistry, VCh.

d) Workup of the Reaction Mixture

The reaction end product thus formed can theoretically be purified further, or the solvent can be removed. Optionally, excess reagent, for example excess epoxide, amine and/or alcohol, can be removed. This can be accomplished, for example, by introducing nitrogen at standard pressure or under reduced pressure. In order to improve the further processability of the products, however, it is also possible to add solvents after the reaction, for example solvents of the Solvesso series, 2-ethylhexanol, or essentially aliphatic solvents. Usually, however, this is not absolutely necessary, and so the reaction product is usable without further purification as an additive, optionally after blending with further additive components (see below).

B) Further Additive Components

The fuel additized with the inventive quaternized additive is a gasoline fuel or especially a middle distillate fuel, in particular a diesel fuel.

The fuel may comprise further customary additives to improve efficacy and/or suppress wear.

In the case of diesel fuels, these are primarily customary detergent additives, carrier oils, cold flow improvers, lubricity improvers, corrosion inhibitors, demulsifiers, dehazers, antifoams, cetane number improvers, combustion improvers, antioxidants or stabilizers, antistats, metallocenes, metal deactivators, dyes and/or solvents.

In the case of gasoline fuels, these are in particular lubricity improvers (friction modifiers), corrosion inhibitors, demulsifiers, dehazers, antifoams, combustion improvers, antioxidants or stabilizers, antistats, metallocenes, metal deactivators, dyes and/or solvents.

Typical examples of suitable coadditives are listed in the following section:

B1) Detergent Additives

The customary detergent additives are preferably amphiphilic substances which possess at least one hydrophobic hydrocarbon radical with a number-average molecular weight ($M_n$) of 85 to 20 000 and at least one polar moiety selected from:
(Da) mono- or polyamino groups having up to 6 nitrogen atoms, at least one nitrogen atom having basic properties;
(Db) nitro groups, optionally in combination with hydroxyl groups;
(Dc) hydroxyl groups in combination with mono- or polyamino groups, at least one nitrogen atom having basic properties;
(Dd) carboxyl groups or the alkali metal or alkaline earth metal salts thereof;
(De) sulfonic acid groups or the alkali metal or alkaline earth metal salts thereof;
(Df) polyoxy-$C_2$- to $C_4$-alkylene moieties terminated by hydroxyl groups, mono- or polyamino groups, at least one nitrogen atom having basic properties, or by carbamate groups;
(Dg) carboxylic ester groups;
(Dh) moieties derived from succinic anhydride and having hydroxyl and/or amino and/or amido and/or imido groups; and/or
(Di) moieties obtained by Mannich reaction of substituted phenols with aldehydes and mono- or polyamines.

The hydrophobic hydrocarbon radical in the above detergent additives, which ensures the adequate solubility in the fuel, has a number-average molecular weight ($M_n$) of 85 to 20000, preferably of 113 to 10000, more preferably of 300 to 5000, even more preferably of 300 to 3000, even more especially preferably of 500 to 2500 and especially of 700 to 2500, in particular of 800 to 1500. Useful typical hydrophobic hydrocarbon radicals, especially in conjunction with the polar moieties, are especially polypropenyl, polybutenyl and polyisobutenyl radicals with a number-average molecular weight $M_n$ of preferably in each case 300 to 5000, more preferably 300 to 3000, even more preferably 500 to 2500, even more especially preferably 700 to 2500 and especially 800 to 1500 into consideration.

Examples of the above groups of detergent additives include the following:

Additives comprising mono- or polyamino groups (Da) are preferably polyalkenemono- or polyalkenepolyamines based on polypropene or on high-reactivity (i.e. having predominantly terminal double bonds) or conventional (i.e. having predominantly internal double bonds) polybutene or polyisobutene with $M_n$=300 to 5000, more preferably 500 to 2500 and especially 700 to 2500. Such additives based on high-reactivity polyisobutene, which can be prepared from the polyisobutene which may comprise up to 20% by weight of n-butene units by hydroformylation and reductive amination with ammonia, monoamines or polyamines such as dimethylaminopropylamine, ethylenediamine, diethylenetriamine, triethylenetetramine or tetraethylenepentamine, are known especially from EP-A 244 616. When polybutene or polyisobutene having predominantly internal double bonds (usually in the β and γ positions) are used as starting materials in the preparation of the additives, a possible preparative route is by chlorination and subsequent amination or by oxidation of the double bond with air or ozone to give the carbonyl or carboxyl compound and subsequent amination under reductive (hydrogenating) conditions. The amines used here for the amination may be, for example, ammonia, monoamines or the abovementioned polyamines. Corresponding additives based on polypropene are described more particularly in WO-A 94/24231.

Further particular additives comprising monoamino groups (Da) are the hydrogenation products of the reaction products of polyisobutenes having an average degree of polymerization P=5 to 100 with nitrogen oxides or mixtures of nitrogen oxides and oxygen, as described more particularly in WO-A 97/03946.

Further particular additives comprising monoamino groups (Da) are the compounds obtainable from polyisobutene epoxides by reaction with amines and subsequent dehydration and reduction of the amino alcohols, as described more particularly in DE-A 196 20 262.

Additives comprising nitro groups (Db), optionally in combination with hydroxyl groups, are preferably reaction products of polyisobutenes having an average degree of polymerization P=5 to 100 or 10 to 100 with nitrogen oxides or mixtures of nitrogen oxides and oxygen, as described more particularly in WO-A 96/03367 and in WO-A 96/03479. These reaction products are generally mixtures of pure nitropolyisobutenes (e.g. α,β-dinitropolyisobutene) and mixed hydroxynitropolyisobutenes (e.g. α-nitro-β-hydroxypolyisobutene).

Additives comprising hydroxyl groups in combination with mono- or polyamino groups (Dc) are especially reaction products of polyisobutene epoxides obtainable from polyisobutene having preferably predominantly terminal double bonds and $M_n$=300 to 5000, with ammonia or mono- or polyamines, as described more particularly in EP-A 476 485.

Additives comprising carboxyl groups or their alkali metal or alkaline earth metal salts (Dd) are preferably copolymers of $C_2$- to $C_{40}$-olefins with maleic anhydride which have a total molar mass of 500 to 20000 and wherein some or all of the carboxyl groups have been converted to the alkali metal or alkaline earth metal salts and any remainder of the carboxyl groups has been reacted with alcohols or amines. Such additives are disclosed more particularly by EP-A 307 815. Such additives serve mainly to prevent valve seat wear and can, as described in WO-A 87/01126, advantageously be used in combination with customary fuel detergents such as poly(iso)buteneamines or polyetheramines.

Additives comprising sulfonic acid groups or their alkali metal or alkaline earth metal salts (De) are preferably alkali metal or alkaline earth metal salts of an alkyl sulfosuccinate, as described more particularly in EP-A 639 632. Such additives serve mainly to prevent valve seat wear and can be used advantageously in combination with customary fuel detergents such as poly(iso)buteneamines or polyetheramines.

Additives comprising polyoxy-$C_1$-$C_4$-alkylene moieties (Df) are preferably polyethers or polyetheramines which are obtainable by reaction of $C_2$- to $C_{60}$-alkanols, $C_6$- to $C_{30}$-alkanediols, mono- or di-$C_2$- to $C_{30}$-alkylamines, $C_1$- to $C_{30}$-alkylcyclohexanols or $C_1$- to $C_{30}$-alkylphenols with 1 to 30 mol of ethylene oxide and/or propylene oxide and/or butylene oxide per hydroxyl group or amino group and, in the case of the polyetheramines, by subsequent reductive amination with ammonia, monoamines or polyamines. Such products are described more particularly in EP-A 310 875, EP-A 356 725, EP-A 700 985 and U.S. Pat. No. 4,877,416. In the case of polyethers, such products also have carrier oil properties. Typical examples thereof are tridecanol butoxylates or isotridecanol butoxylates, isononylphenol butoxylates and also polyisobutenol butoxylates and propoxylates, and also the corresponding reaction products with ammonia.

Additives comprising carboxylic ester groups (Dg) are preferably esters of mono-, di- or tricarboxylic acids with long-chain alkanols or polyols, especially those having a minimum viscosity of 2 mm²/s at 100° C., as described more particularly in DE-A 38 38 918. The mono-, di- or tricarboxylic acids used may be aliphatic or aromatic acids, and particularly suitable ester alcohols or ester polyols are long-chain representatives having, for example, 6 to 24 carbon atoms. Typical representatives of the esters are adipates, phthalates, isophthalates, terephthalates and trimellitates of isooctanol, of isononanol, of isodecanol and of isotridecanol. Such products also satisfy carrier oil properties.

Additives comprising moieties derived from succinic anhydride and having hydroxyl and/or amino and/or amido and/or especially imido groups (Dh) are preferably corresponding derivatives of alkyl- or alkenyl-substituted succinic anhydride and especially the corresponding derivatives of polyisobutenylsuccinic anhydride which are obtainable by reacting conventional or high-reactivity polyisobutene having $M_n$=preferably 300 to 5000, more preferably 300 to 3000, even more preferably 500 to 2500, even more especially preferably 700 to 2500 and especially 800 to 1500, with maleic anhydride by a thermal route in an ene reaction or via the chlorinated polyisobutene. The moieties having hydroxyl and/or amino and/or amido and/or imido groups are, for example, carboxylic acid groups, acid amides of monoamines, acid amides of di- or polyamines which, in addition to the amide function, also have free amine groups, succinic acid derivatives having an acid and an amide function, carboximides with monoamines, carboximides with di- or polyamines which, in addition to the imide function, also have free amine groups, or diimides which are formed by the reaction of di- or polyamines with two succinic acid derivatives. In the presence of imido moieties D(h), the further detergent additive in the context of the present invention is, however, used only up to a maximum of 100% of the weight of compounds with betaine structure. Such fuel additives are common knowledge and are described, for example, in documents (1) and (2). They are preferably the reaction products of alkyl- or alkenyl-substituted succinic acids or derivatives thereof with amines and more preferably the reaction products of polyisobutenyl-substituted succinic acids or derivatives thereof with amines. Of particular interest in this context are reaction products with aliphatic polyamines (polyalkyleneimines) such as especially ethylenediamine, diethylenetriamine, triethylenetetramine, tetraethylenepentamine, pentaethylenehexamine and hexaethyleneheptamine, which have an imide structure.

Additives comprising moieties (Di) obtained by Mannich reaction of substituted phenols with aldehydes and mono- or polyamines are preferably reaction products of polyisobutene-substituted phenols with formaldehyde and mono- or polyamines such as ethylenediamine, diethylenetriamine, triethylenetetramine, tetraethylenepentamine or dimethylaminopropylamine. The polyisobutenyl-substituted phenols may originate from conventional or high-reactivity polyisobutene having $M_n$=300 to 5000. Such "polyisobutene Mannich bases" are described more particularly in EP-A 831 141.

One or more of the detergent additives mentioned can be added to the fuel in such an amount that the dosage rate of these detergent additives is preferably 25 to 2500 ppm by weight, especially 75 to 1500 ppm by weight, in particular 150 to 1000 ppm by weight.

B2) Carrier Oils

Carrier oils additionally used may be of mineral or synthetic nature. Suitable mineral carrier oils are fractions obtained in crude oil processing, such as brightstock or base oils having viscosities, for example, from the SN 500-2000 class; but also aromatic hydrocarbons, paraffinic hydrocarbons and alkoxyalkanols. Likewise useful is a fraction which is obtained in the refining of mineral oil and is known as "hydrocrack oil" (vacuum distillate cut having a boiling range of from about 360 to 500° C., obtainable from natural mineral oil which has been catalytically hydrogenated under high pressure and isomerized and also deparaffinized). Likewise suitable are mixtures of the abovementioned mineral carrier oils.

Examples of suitable synthetic carrier oils are polyolefins (polyalphaolefins or polyinternalolefins), (poly)esters, (poly)alkoxylates, polyethers, aliphatic polyetheramines, alkylphenol-started polyethers, alkylphenol-started polyetheramines and carboxylic esters of long-chain alkanols.

Examples of suitable polyolefins are olefin polymers having $M_n$=400 to 1800, in particular based on polybutene or polyisobutene (hydrogenated or unhydrogenated).

Examples of suitable polyethers or polyetheramines are preferably compounds comprising polyoxy-$C_2$- to $C_4$-alkylene moieties obtainable by reacting $C_2$- to $C_{60}$-alkanols, $C_6$- to $C_{30}$-alkanediols, mono- or di-$C_2$- to $C_{30}$-alkylamines, $C_1$- to $C_{30}$-alkylcyclohexanols or $C_1$- to $C_{30}$-alkylphenols with 1 to 30 mol of ethylene oxide and/or propylene oxide and/or butylene oxide per hydroxyl group or amino group, and, in the case of the polyetheramines, by subsequent reductive amination with ammonia, monoamines or polyamines. Such products are described more particularly in EP-A 310 875, EP-A 356 725, EP-A 700 985 and U.S. Pat. No. 4,877,416. For example, the polyetheramines used may be poly-$C_2$- to $C_6$-alkylene oxide amines or functional derivatives thereof. Typical examples thereof are tridecanol butoxylates or isotridecanol butoxylates, isononylphenol butoxylates and also polyisobutenol butoxylates and propoxylates, and also the corresponding reaction products with ammonia.

Examples of carboxylic esters of long-chain alkanols are more particularly esters of mono-, di- or tricarboxylic acids with long-chain alkanols or polyols, as described more particularly in DE-A 38 38 918. The mono-, di- or tricarboxylic acids used may be aliphatic or aromatic acids; particularly suitable ester alcohols or ester polyols are long-chain representatives having, for example, 6 to 24 carbon atoms. Typical representatives of the esters are adipates, phthalates, isophthalates, terephthalates and trimellitates of isooctanol, isononanol, isodecanol and isotridecanol, for example di(n- or isotridecyl) phthalate.

Further suitable carrier oil systems are described, for example, in DE-A 38 26 608, DE-A 41 42 241, DE-A 43 09 074, EP-A 452 328 and EP-A 548 617.

Examples of particularly suitable synthetic carrier oils are alcohol-started polyethers having about 5 to 35, preferably about 5 to 30, more preferably 10 to 30 and especially 15 to 30 $C_3$- to $C_6$-alkylene oxide units, for example propylene oxide, n-butylene oxide and isobutylene oxide units, or mixtures thereof, per alcohol molecule. Nonlimiting examples of suitable starter alcohols are long-chain alkanols or phenols substituted by long-chain alkyl in which the long-chain alkyl radical is especially a straight-chain or branched $C_6$- to $C_{18}$-alkyl radical. Particular examples include tridecanol and nonylphenol. Particularly preferred alcohol-started polyethers are the reaction products (polyetherification products) of monohydric aliphatic $C_6$- to $C_{18}$-alcohols with $C_3$- to $C_6$-alkylene oxides. Examples of monohydric aliphatic $C_6$-$C_{18}$-alcohols are hexanol, heptanol, octanol, 2-ethylhexanol, nonyl alcohol, decanol, 3-propylheptanol, undecanol, dodecanol, tridecanol, tetradecanol, pentadecanol, hexadecanol, octadecanol and the constitutional and positional isomers thereof. The alcohols can be used either in the form of the pure isomers or in the form of technical grade mixtures. A particularly preferred alcohol is tridecanol. Examples of $C_3$- to $C_6$-alkylene oxides are propylene oxide, such as 1,2-propylene oxide, butylene oxide, such as 1,2-butylene oxide, 2,3-butylene oxide, isobutylene oxide or tetrahydrofuran, pentylene oxide and hexylene oxide. Particular preference among these is given to $C_3$- to $C_4$-alkylene oxides, i.e. propylene oxide such as 1,2-propylene oxide and butylene oxide such as 1,2-butylene oxide, 2,3-butylene oxide and isobutylene oxide. Especially butylene oxide is used.

Further suitable synthetic carrier oils are alkoxylated alkylphenols, as described in DE-A 10 102 913.

Particular carrier oils are synthetic carrier oils, particular preference being given to the above-described alcohol-started polyethers.

The carrier oil or the mixture of different carrier oils is added to the fuel in an amount of preferably 1 to 1000 ppm by weight, more preferably of 10 to 500 ppm by weight and especially of 20 to 100 ppm by weight.

B3) Cold Flow Improvers

Suitable cold flow improvers are in principle all organic compounds which are capable of improving the flow performance of middle distillate fuels or diesel fuels under cold conditions. For the intended purpose, they must have sufficient oil solubility. More particularly, useful cold flow improvers for this purpose are the cold flow improvers (middle distillate flow improvers, MDFIs) typically used in the case of middle distillates of fossil origin, i.e. in the case of customary mineral diesel fuels. However, it is also possible to use organic compounds which partly or predominantly have the properties of a wax antisettling additive (WASA) when used in customary diesel fuels. They can also act partly or predominantly as nucleators. It is also possible to use mixtures of organic compounds effective as MDFIs and/or effective as WASAs and/or effective as nucleators.

The cold flow improver is typically selected from (K1) copolymers of a $C_2$- to $C_{40}$-olefin with at least one further ethylenically unsaturated monomer;

(K2) comb polymers;

(K3) polyoxyalkylenes;

(K4) polar nitrogen compounds;

(K5) sulfocarboxylic acids or sulfonic acids or derivatives thereof; and (K6) poly(meth)acrylic esters.

It is possible to use either mixtures of different representatives from one of the particular classes (K1) to (K6) or mixtures of representatives from different classes (K1) to (K6).

Suitable $C_2$- to $C_{40}$-olefin monomers for the copolymers of class (K1) are, for example, those having 2 to 20 and especially 2 to 10 carbon atoms, and 1 to 3 and preferably 1 or 2 carbon-carbon double bonds, especially having one carbon-carbon double bond.

In the latter case, the carbon-carbon double bond may be arranged either terminally (α-olefins) or internally. However, preference is given to α-olefins, particular preference to α-olefins having 2 to 6 carbon atoms, for example propene, 1-butene, 1-pentene, 1-hexene and in particular ethylene.

In the copolymers of class (K1), the at least one further ethylenically unsaturated monomer is preferably selected from alkenyl carboxylates, (meth)acrylic esters and further olefins.

When further olefins are also copolymerized, they are preferably higher in molecular weight than the abovementioned $C_2$- to $C_{40}$-olefin base monomers. When, for example, the olefin base monomer used is ethylene or propene, suitable further olefins are especially $C_{10}$- to $C_{40}$-α-olefins. Further olefins are in most cases only additionally copolymerized when monomers with carboxylic ester functions are also used.

Suitable (meth)acrylic esters are, for example, esters of (meth)acrylic acid with $C_1$- to $C_{20}$-alkanols, especially $C_1$- to $C_{10}$-alkanols, in particular with methanol, ethanol, propanol, isopropanol, n-butanol, sec-butanol, isobutanol, tertbutanol, pentanol, hexanol, heptanol, octanol, 2-ethylhexanol, nonanol and decanol, and structural isomers thereof.

Suitable alkenyl carboxylates are, for example, $C_2$- to $C_{14}$-alkenyl esters, for example the vinyl and propenyl esters, of carboxylic acids having 2 to 21 carbon atoms, whose hydrocarbyl radical may be linear or branched. Among these, preference is given to the vinyl esters. Among the carboxylic acids with a branched hydrocarbyl radical, preference is given to those whose branch is in the α position to the carboxyl group, and the α-carbon atom is more preferably tertiary, i.e. the carboxylic acid is what is called a neocarboxylic acid. However, the hydrocarbyl radical of the carboxylic acid is preferably linear.

Examples of suitable alkenyl carboxylates are vinyl acetate, vinyl propionate, vinyl butyrate, vinyl 2-ethylhexanoate, vinyl neopentanoate, vinyl hexanoate, vinyl neononanoate, vinyl neodecanoate and the corresponding propenyl esters, preference being given to the vinyl esters. A particularly preferred alkenyl carboxylate is vinyl acetate; typical copolymers of group (K1) resulting therefrom are ethylene-vinyl acetate copolymers ("EVAs"), which are some of the most frequently used.

Ethylene-vinyl acetate copolymers usable particularly advantageously and the preparation thereof are described in WO 99/29748.

Suitable copolymers of class (K1) are also those which comprise two or more different alkenyl carboxylates in copolymerized form, which differ in the alkenyl function and/or in the carboxylic acid group. Likewise suitable are copolymers which, as well as the alkenyl carboxylate(s), comprise at least one olefin and/or at least one (meth)acrylic ester in copolymerized form.

Terpolymers of a $C_2$- to $C_{40}$-α-olefin, a $C_1$- to $C_{20}$-alkyl ester of an ethylenically unsaturated monocarboxylic acid having 3 to 15 carbon atoms and a $C_2$- to $C_{14}$-alkenyl ester of a saturated monocarboxylic acid having 2 to 21 carbon atoms are also suitable as copolymers of class (K1). Terpolymers of this kind are described in WO 2005/054314. A typical terpolymer of this kind is formed from ethylene, 2-ethylhexyl acrylate and vinyl acetate.

The at least one or the further ethylenically unsaturated monomer(s) are copolymerized in the copolymers of class (K1) in an amount of preferably 1 to 50% by weight, especially 10 to 45% by weight and in particular 20 to 40% by weight, based on the overall copolymer. The main proportion in terms of weight of the monomer units in the copolymers of class (K1) therefore originates generally from the $C_2$- to $C_{40}$ base olefins.

The copolymers of class (K1) preferably have a number-average molecular weight $M_n$ of 1000 to 20000, more preferably of 1000 to 10000 and especially of 1000 to 8000.

Typical comb polymers of component (K2) are, for example, obtainable by the copolymerization of maleic anhydride or fumaric acid with another ethylenically unsaturated monomer, for example with an α-olefin or an unsaturated ester, such as vinyl acetate, and subsequent esterification of the anhydride or acid function with an alcohol having at least 10 carbon atoms. Further suitable comb polymers are copolymers of α-olefins and esterified comonomers, for example esterified copolymers of styrene and maleic anhydride or esterified copolymers of styrene and fumaric acid. Suitable comb polymers may also be polyfumarates or polymaleates. Homo- and copolymers of vinyl ethers are also suitable comb polymers. Comb polymers suitable as components of class (K2) are, for example, also those described in WO 2004/035715 and in "Comb-Like Polymers, Structure and Properties", N. A. Platé and V. P. Shibaev, J. Poly. Sci. Macromolecular Revs. 8, pages 117 to 253 (1974). Mixtures of comb polymers are also suitable.

Polyoxyalkylenes suitable as components of class (K3) are, for example, polyoxyalkylene esters, polyoxyalkylene ethers, mixed polyoxyalkylene ester/ethers and mixtures thereof. These polyoxyalkylene compounds preferably comprise at least one linear alkyl group, preferably at least two linear alkyl groups, each having 10 to 30 carbon atoms and a polyoxyalkylene group having a number-average molecular weight of up to 5000. Such polyoxyalkylene compounds are described, for example, in EP A 061 895 and also in U.S. Pat. No. 4,491,455. Particular polyoxyalkylene compounds are based on polyethylene glycols and polypropylene glycols having a number-average molecular weight of 100 to 5000. Additionally suitable are polyoxyalkylene mono- and diesters of fatty acids having 10 to 30 carbon atoms, such as stearic acid or behenic acid.

Polar nitrogen compounds suitable as components of class (K4) may be either ionic or nonionic and preferably have at least one substituent, especially at least two substituents, in the form of a tertiary nitrogen atom of the general formula >$NR^7$ in which $R^7$ is a $C_8$- to $C_{40}$-hydrocarbyl radical. The nitrogen substituents may also be quaternized, i.e. be in cationic form. An example of such nitrogen compounds is that of ammonium salts and/or amides which are obtainable by the reaction of at least one amine substituted by at least one hydrocarbyl radical with a carboxylic acid having 1 to 4 carboxyl groups or with a suitable derivative thereof. The amines preferably comprise at least one linear $C_8$- to $C_{40}$-alkyl radical. Primary amines suitable for preparing the polar nitrogen compounds mentioned are, for example, octylamine, nonylamine, decylamine, undecylamine, dodecylamine, tetradecylamine and the higher linear homologs; secondary amines suitable for this purpose are, for example, dioctadecylamine and methylbehenylamine. Also suitable for this purpose are amine mixtures, especially amine mixtures obtainable on the industrial scale, such as fatty amines or hydrogenated tallamines, as described, for example, in Ullmann's Encyclopedia of Industrial Chemistry, 6th Edition, "Amines, aliphatic" chapter. Acids suitable for the reaction are, for example, cyclohexane-1,2-dicarboxylic acid, cyclohexene-1,2-dicarboxylic acid, cyclopentane-1,2-dicarboxylic acid, naphthalenedicarboxylic acid, phthalic acid, isophthalic acid, terephthalic acid, and succinic acids substituted by long-chain hydrocarbyl radicals.

More particularly, the component of class (K4) is an oil-soluble reaction product of poly($C_2$- to $C_{20}$-carboxylic acids) having at least one tertiary amino group with primary or secondary amines. The poly($C_2$- to -$C_{20}$-carboxylic acids) which have at least one tertiary amino group and form the basis of this reaction product comprise preferably at least 3 carboxyl groups, especially 3 to 12 and in particular 3 to 5 carboxyl groups. The carboxylic acid units in the polycarboxylic acids have preferably 2 to 10 carbon atoms, and are especially acetic acid units. The carboxylic acid units are suitably bonded to the polycarboxylic acids, usually via one or more carbon and/or nitrogen atoms. They are preferably attached to tertiary nitrogen atoms which, in the case of a plurality of nitrogen atoms, are bonded via hydrocarbon chains.

The component of class (K4) is preferably an oil-soluble reaction product based on poly($C_2$- to $C_{20}$-carboxylic acids) which have at least one tertiary amino group and are of the general formula IIa or IIb

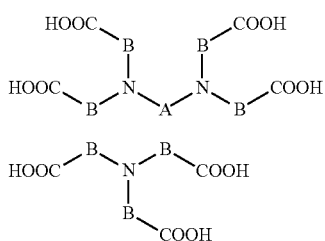

(IIa)

(IIb)

in which the variable A represents a straight-chain or branched $C_2$- to $C_6$-alkylene group or the moiety of the formula III

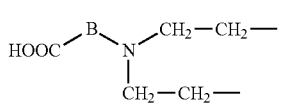

(III)

and the variable B denotes a $C_1$- to $C_{19}$-alkylene group. The compounds of the general formulae IIa and IIb especially have the properties of a WASA.

Moreover, the preferred oil-soluble reaction product of component (K4), especially that of the general formula IIa or IIb, is an amide, an amide-ammonium salt or an ammonium salt in which no, one or more carboxylic acid groups have been converted to amide groups.

Straight-chain or branched $C_2$- to $C_6$-alkylene groups of the variable A are, for example, 1,1-ethylene, 1,2-propylene, 1,3-propylene, 1,2-butylene, 1,3-butylene, 1,4-butylene, 2-methyl-1,3-propylene, 1,5-pentylene, 2-methyl-1,4-butylene, 2,2-dimethyl-1,3-propylene, 1,6-hexylene (hexamethylene) and especially 1,2-ethylene. The variable A comprises preferably 2 to 4 and especially 2 or 3 carbon atoms.

$C_1$- to $C_{19}$-alkylene groups of the variable B are, for example, 1,2-ethylene, 1,3-propylene, 1,4-butylene, hexamethylene, octamethylene, decamethylene, dodecamethylene, tetradecamethylene, hexadecamethylene, octadecamethylene, nonadecamethylene and especially methylene. The variable B comprises preferably 1 to 10 and especially 1 to 4 carbon atoms.

The primary and secondary amines as a reaction partner for the polycarboxylic acids to form component (K4) are typically monoamines, especially aliphatic monoamines. These primary and secondary amines may be selected from a multitude of amines which bear hydrocarbyl radicals which may optionally be bonded to one another.

These parent amines of the oil-soluble reaction products of component (K4) are usually secondary amines and have the general formula $HN(R^8)_2$ in which the two variables $R^8$ are each independently straight-chain or branched $C_{10}$- to $C_{30}$-alkyl radicals, especially $C_{14}$- to $C_{24}$-alkyl radicals. These relatively long-chain alkyl radicals are preferably straight-chain or only slightly branched. In general, the secondary amines mentioned, with regard to their relatively long-chain alkyl radicals, derive from naturally occurring fatty acids and from derivatives thereof. The two $R^8$ radicals are preferably identical.

The secondary amines mentioned may be bonded to the polycarboxylic acids by means of amide structures or in the form of the ammonium salts; it is also possible for only a portion to be present as amide structures and another portion as ammonium salts. Preferably only few, if any, free acid groups are present. The oil-soluble reaction products of component (K4) are preferably present completely in the form of the amide structures.

Typical examples of such components (K4) are reaction products of nitrilotriacetic acid, of ethylenediaminetetraacetic acid or of propylene-1,2-diaminetetraacetic acid with in each case 0.5 to 1.5 mol per carboxyl group, especially 0.8 to 1.2 mol per carboxyl group, of dioleylamine, dipalmitamine, dicocoamine, distearylamine, dibehenylamine or especially ditallamine. A particularly preferred component (K4) is the reaction product of 1 mol of ethylenediaminetetraacetic acid and 4 mol of hydrogenated ditallamine.

Further typical examples of component (K4) include the N,N-dialkylammonium salts of 2-N',N'-dialkylamidobenzoates, for example the reaction product of 1 mol of phthalic anhydride and 2 mol of ditallamine, the latter being hydrogenated or unhydrogenated, and the reaction product of 1 mol of an alkenylspirobislactone with 2 mol of a dialkylamine, for example ditallamine and/or tallamine, the latter two being hydrogenated or unhydrogenated.

Further typical structure types for the component of class (K4) are cyclic compounds with tertiary amino groups or condensates of long-chain primary or secondary amines with carboxylic acid-containing polymers, as described in WO 93/18115.

Sulfocarboxylic acids, sulfonic acids or derivatives thereof which are suitable as cold flow improvers of the component of class (K5) are, for example, the oil-soluble carboxamides and carboxylic esters of ortho-sulfobenzoic acid, in which the sulfonic acid function is present as a sulfonate with alkyl-substituted ammonium cations, as described in EP-A 261 957.

Poly(meth)acrylic esters suitable as cold flow improvers of the component of class (K6) are either homo- or copolymers of acrylic and methacrylic esters. Preference is given to copolymers of at least two different (meth)acrylic esters which differ with regard to the esterified alcohol. The copolymer optionally comprises another different olefinically unsaturated monomer in copolymerized form. The weight-average molecular weight of the polymer is preferably 50000 to 500000. A particularly preferred polymer is a copolymer of methacrylic acid and methacrylic esters of saturated $C_{14}$- and $C_{15}$-alcohols, the acid groups having been neutralized with hydrogenated tallamine. Suitable poly (meth)acrylic esters are described, for example, in WO 00/44857.

The cold flow improver or the mixture of different cold flow improvers is added to the middle distillate fuel or diesel fuel in a total amount of preferably 10 to 5000 ppm by weight, more preferably of 20 to 2000 ppm by weight, even more preferably of 50 to 1000 ppm by weight and especially of 100 to 700 ppm by weight, for example of 200 to 500 ppm by weight.

B4) Lubricity Improvers

Suitable lubricity improvers or friction modifiers are based typically on fatty acids or fatty acid esters. Typical examples are tall oil fatty acid, as described, for example, in WO 98/004656, and glyceryl monooleate. The reaction products, described in U.S. Pat. No. 6,743,266 B2, of natural or synthetic oils, for example triglycerides, and alkanolamines are also suitable as such lubricity improvers.

B5) Corrosion Inhibitors

Suitable corrosion inhibitors are, for example, succinic esters, in particular with polyols, fatty acid derivatives, for example oleic esters, oligomerized fatty acids, substituted ethanolamines, and products sold under the trade name RC 4801 (Rhein Chemie Mannheim, Germany) or HiTEC 536 (Ethyl Corporation).

B6) Demulsifiers

Suitable demulsifiers are, for example, the alkali metal or alkaline earth metal salts of alkyl-substituted phenol- and naphthalenesulfonates and the alkali metal or alkaline earth metal salts of fatty acids, and also neutral compounds such as alcohol alkoxylates, e.g. alcohol ethoxylates, phenol alkoxylates, e.g. tert-butylphenol ethoxylate or tert-pentylphenol ethoxylate, fatty acids, alkylphenols, condensation products of ethylene oxide (EO) and propylene oxide (PO), for example including in the form of EO/PO block copolymers, polyethyleneimines or else polysiloxanes.

B7) Dehazers

Suitable dehazers are, for example, alkoxylated phenol-formaldehyde condensates, for example the products available under the trade names NALCO 7D07 (Nalco) and TOLAD 2683 (Petrolite).

B8) Antifoams

Suitable antifoams are, for example, polyether-modified polysiloxanes, for example the products available under the trade names TEGOPREN 5851 (Goldschmidt), Q 25907 (Dow Corning) and RHODOSIL (Rhone Poulenc).

B9) Cetane Number Improvers

Suitable cetane number improvers are, for example, aliphatic nitrates such as 2-ethylhexyl nitrate and cyclohexyl nitrate and peroxides such as di-tert-butyl peroxide.

B10) Antioxidants

Suitable antioxidants are, for example substituted phenols, such as 2,6-di-tert-butylphenol and 6-di-tert-butyl-3-methylphenol, and also phenylenediamines such as N,N'-di-sec-butyl-p-phenylenediamine.

B11) Metal Deactivators

Suitable metal deactivators are, for example, salicylic acid derivatives such as N,N'-disalicylidene-1,2-propanediamine.

B12) Solvents

Suitable solvents are, for example, nonpolar organic solvents such as aromatic and aliphatic hydrocarbons, for example toluene, xylenes, white spirit and products sold under the trade names SHELLSOL (Royal Dutch/Shell Group) and EXXSOL (ExxonMobil), and also polar organic solvents, for example, alcohols such as 2-ethylhexanol, decanol and isotridecanol. Such solvents are usually added to the diesel fuel together with the aforementioned additives and coadditives, which they are intended to dissolve or dilute for better handling.

C) Fuels

The inventive additive is outstandingly suitable as a fuel additive and can be used in principle in any fuels. It brings about a whole series of advantageous effects in the operation of internal combustion engines with fuels. Preference is given to using the inventive quaternized additive in middle distillate fuels, especially diesel fuels.

The present invention therefore also provides fuels, especially middle distillate fuels, with a content of the inventive quaternized additive which is effective as an additive for achieving advantageous effects in the operation of internal combustion engines, for example of diesel engines, especially of direct injection diesel engines, in particular of diesel engines with common rail injection systems. This effective content (dosage rate) is generally 10 to 5000 ppm by weight, preferably 20 to 1500 ppm by weight, especially 25 to 1000 ppm by weight, in particular 30 to 750 ppm by weight, based in each case on the total amount of fuel.

Middle distillate fuels such as diesel fuels or heating oils are preferably mineral oil raffinates which typically have a boiling range from 100 to 400° C. These are usually distillates having a 95% point up to 360° C. or even higher. These may also be what is called "ultra low sulfur diesel" or "city diesel", characterized by a 95% point of, for example, not more than 345° C. and a sulfur content of not more than 0.005% by weight or by a 95% point of, for example, 285° C. and a sulfur content of not more than 0.001% by weight. In addition to the mineral middle distillate fuels or diesel fuels obtainable by refining, those obtainable by coal gasification or gas liquefaction ["gas to liquid" (GTL) fuels] or by biomass liquefaction ["biomass to liquid" (BTL) fuels] are also suitable. Also suitable are mixtures of the aforementioned middle distillate fuels or diesel fuels with renewable fuels, such as biodiesel or bioethanol.

The qualities of the heating oils and diesel fuels are laid down in detail, for example, in DIN 51603 and EN 590 (cf. also Ullmann's Encyclopedia of Industrial Chemistry, 5th edition, Volume A12, p. 617 ff.).

In addition to the use thereof in the abovementioned middle distillate fuels of fossil, vegetable or animal origin, which are essentially hydrocarbon mixtures, the inventive quaternized additive can also be used in mixtures of such middle distillates with biofuel oils (biodiesel). Such mixtures are also encompassed by the term "middle distillate fuel" in the context of the present invention. They are commercially available and usually comprise the biofuel oils in minor amounts, typically in amounts of 1 to 30% by weight, especially of 3 to 10% by weight, based on the total amount of middle distillate of fossil, vegetable or animal origin and biofuel oil.

Biofuel oils are generally based on fatty acid esters, preferably essentially on alkyl esters of fatty acids which derive from vegetable and/or animal oils and/or fats. Alkyl esters are typically understood to mean lower alkyl esters, especially $C_1$- to $C_4$-alkyl esters, which are obtainable by transesterifying the glycerides which occur in vegetable and/or animal oils and/or fats, especially triglycerides, by means of lower alcohols, for example ethanol or in particular methanol ("FAME"). Typical lower alkyl esters based on vegetable and/or animal oils and/or fats, which find use as a biofuel oil or components thereof, are, for example, sunflower methyl ester, palm oil methyl ester ("PME"), soya oil methyl ester ("SME") and especially rapeseed oil methyl ester ("RME").

The middle distillate fuels or diesel fuels are more preferably those having a low sulfur content, i.e. having a sulfur content of less than 0.05% by weight, preferably of less than 0.02% by weight, more particularly of less than 0.005% by weight and especially of less than 0.001% by weight of sulfur.

Useful gasoline fuels include all commercial gasoline fuel compositions. One typical representative which shall be mentioned here is the Eurosuper base fuel to EN 228, which is customary on the market. In addition, gasoline fuel compositions of the specification according to WO 00/47698 are also possible fields of use for the present invention.

The inventive quaternized additive is especially suitable as a fuel additive in fuel compositions, especially in diesel fuels, for overcoming the problems outlined at the outset in direct injection diesel engines, in particular in those with common rail injection systems.

The invention is now illustrated in detail by the working examples which follow. More particularly, the test methods specified hereinafter are part of the general disclosure of the application and are not restricted to the specific working examples.

EXPERIMENTAL

A. General Test Methods

Engine Tests

1. XUD9 Test—Determination of Flow Restriction

The procedure was according to the standard provisions of CEC F-23-01.

2. DW10 Test—Determination of Power Loss as a Result of Injector Deposits in the Common Rail Diesel Engine 2.1. DW10-KC—Keep-Clean Test The keep-clean test is based on CEC test procedure F-098-08 Issue 5. This is done using the same test setup and engine type (PEUGEOT DW10) as in the CEC procedure.

Alteration and Special Features:

In the tests, cleaned injectors were used. The cleaning time in the ultrasound bath in water+10% Superdecontamine (Intersciences, Brussels) at 60° C. was 4 h.

Test Run Times:

The test run time was 12 h without shutdown phases. The one-hour test cycle from CEC F-098-08, shown in FIG. 2, was run through 12 times.

Power Determination:

The initial power P0,KC [kW] is calculated from the measured torque at full load 4000/min directly after the test has started and the engine has run hot. The procedure is described in Issue 5 of the test procedure (CEC F-98-08). This is done using the same test setup and the PEUGEOT DW10 engine type.

The final power (Pend,KC) is determined in the 12th cycle in stage 12 (see table, FIG. 2). Here too, the operation point is full load 4000/min. Pend,KC [kW] is calculated from the torque measured.

The power loss in the KC test is calculated as follows:

$$Powerloss, KC[\%] = \left(1 - \frac{Pend, KC}{P0, KC}\right) * 100$$

2.2. DW10 Dirty-Up Clean-Up (DU-CU)

The DU-CU test is based on CEC test procedure F-098-08 Issue 5. The procedure is described in Issue 5 of the test procedure (CEC F-98-08). This is done using the same test setup and the PEUGEOT DW10 engine type.

The DU-CU test consists of two individual tests which are run in succession. The first test serves to form deposits (DU), the second to remove the deposits (CU). After the DU, the power loss is determined. After the end of the DU run, the engine is not operated for at least 8 hours and is cooled to ambient temperature. Thereafter, the CU fuel is used to start the CU without deinstalling and cleaning the injectors. The deposits and power loss ideally decline over the course of the CU test.

Alteration and Special Features:

Cleaned injectors were installed in the engine prior to each DU test. The cleaning time in the ultrasound bath at 60° C., in water+10% Superdecontamine (Intersciences, Brussels), was 4 h.

Test Run Times:

The test run time was 12 h for the DU and 12 h for the CU. The engine was operated in the DU and CU tests without shutdown phases.

The one-hour test cycle from CEC F-098-08, shown in FIG. 2, was run through 12 times in each case.

Power Determination:

The initial power P0,du [kW] is calculated from the measured torque at full load 4000/min directly after the test has started and the engine has run hot. The procedure is likewise described in Issue 5 of the test procedure.

The final power (Pend,du) is determined in the 12th cycle in stage 12 (see table above). Here too, the operation point is full load 4000/min. Pend,du [kW] is calculated from the torque measured.

The power loss in the DU is calculated as follows:

$$Powerloss, du[\%] = \left(1 - \frac{Pend, du}{P0, du}\right) * 100$$

Clean-Up

The initial power P0,cu [kW] is calculated from the measured torque at full load 4000/min directly after the test has started and the engine has run hot in the CU. The procedure is likewise described in Issue 5 of the test procedure.

The final power (Pend,cu) is determined in the 12th cycle in stage 12 (see table, FIG. 2). Here too, the operation point is full load 4000/min. Pend,cu [kW] is calculated from the torque measured.

The power loss in the CU test is calculated as follows (negative number for the power loss in the cu test means an increase in power)

$$Powerloss, (DU, CU)[\%] = \left(\frac{Pend, du - pend, cu}{P0, du}\right) * 100$$

The fuel used was a commercial diesel fuel from Haltermann (RF-06-03). To artificially induce the formation of deposits at the injectors, 1 ppm by weight of zinc in the form of a zinc didodecanoate solution was added thereto.

3. IDID Test—Determination of Additive Effect on Internal Injector Deposits

The formation of deposits within the injector was characterized by the deviations in the exhaust gas temperatures of the cylinders at the cylinder outlet on cold starting of the DW10 engine.

To promote the formation of deposits, 1 mg/l of sodium salt of an organic acid, 20 mg/l of dodecenylsuccinic acid and 10 mg/l of water were added to the fuel.

The test is conducted as a dirty-up clean-up test (DU-CU). DU-CU is based on CEC test procedure F-098-08 Issue 5.

The DU-CU test consists of two individual tests which are run in succession. The first test serves to form deposits (DU), the second to remove the deposits (CU).

After the DU run, after a rest phase of at least eight hours, a cold start of the engine is conducted, followed by idling for 10 minutes.

Thereafter, the CU fuel is used to start the CU without deinstalling and cleaning the injectors. After the CU run over 8 h, after a rest phase of at least eight hours, a cold start of the engine is conducted, followed by idling for 10 minutes. The evaluation is effected by the comparison of the temperature profiles for the individual cylinders after the cold start in the DU and CU runs.

The IDID test indicates the formation of internal deposits in the injector. The characteristic used in this test is the exhaust gas temperature of the individual cylinders. In an injector system without IDIDs, the exhaust gas temperatures of the cylinders increase homogeneously. In the presence of IDIDs, the exhaust gas temperatures of the individual cylinders do not increase homogeneously and deviate from one another.

The temperature sensors are beyond the cylinder head outlet in the exhaust gas manifold. Significant deviation of the individual cylinder temperatures (e.g. >20° C.) indicates the presence of internal injector deposits (IDIDs).

The tests (DU and CU) are each conducted with run time 8 h. The one-hour test cycle from CEC F-098-08 (see FIG. 1) is run through 8 times in each case. In the event of deviations of the individual cylinder temperatures of greater than 45° C. from the mean for all 4 cylinders, the test is stopped early.

Alteration and special features: Cleaned injectors were installed before the start of each DU test run. The cleaning time in the ultrasound bath at 60° C., in water+10% Superdecontamine, was 4 h.

B. Preparation Examples

Reagents used:
cocoyldimethylamine (N,N-dimethyl-N-C12/14-amine, CAS 68439-70-3 and 112-18-5) having a total amine value of 246 mg KOH/g.
isononanoic acid (CAS 3302-10-1) from BASF.
dimethyl oxalate (CAS 553-90-2) from Aldrich
2-propylheptanol (CAS 10042-59-8) from BASF.
Solvent Naphtha, naphthalene-depleted: Hydrosol A 200 ND, CAS 64742-94-5, from DHC Solvent Chemie GmbH
2-ethylhexylamine (CAS 104-75-6) from BASF
oleylamine (CAS 112-90-3) from Aldrich Comparative Example 1: C12/14-NMe$_3$-Methyl Oxalate (Comparative)

In a 1 l jacketed vessel, a mixture of cocoyldimethylamine (300 g), dimethyl oxalate (233 g) and isononanoic acid (1.1 g) is heated to 120° C. for 24 h. Subsequently, excess dimethyl oxalate is removed on a rotary evaporator at 120° C. under reduced pressure. The product is obtained as a beige solid. $^1$H NMR (CDCl$_3$) confirms the quaternization (δ=3.36 ppm (singlet, RN(C$\underline{H}_3$)$_3$), δ=3.71 ppm (singlet, —O$_2$CCO$_2$CH$_3$)).

Inventive Example 1: C12/14-NMe$_3$-2-Propylheptyl Oxalate (Inventive)

A solution of the product from comparative example 1 (314 g) in 2-propylheptanol (598 g) is heated to 120° C. for 6 h, with distillative removal of volatile methanol while passing a nitrogen stream over. The product is obtained as a solution in 2-propylheptanol. $^1$H NMR (CDCl$_3$; after removal of the solvent at 70° C. under high vacuum) confirms the transesterification.

Inventive Example 2: C12/14-NMe$_3$-2-Ethylhexyl Aminooxoacetate (Inventive)

A solution of the product from comparative example 1 (100 g) in Solvent Naphtha, naphthalene-depleted (85 g), and 2-ethylhexylamine (37.6 g) is heated to 120° C. for 4 h, with distillative removal of volatile methanol while passing a nitrogen stream over. $^1$H NMR (CDCl$_3$; after removal of the solvent at 70° C. under high vacuum) confirms the amidation.

Inventive Example 3: C12/14-NMe$_3$-Oleyl Aminooxoacetate (Inventive)

A solution of the product from comparative example 1 (100 g) in Solvent Naphtha, naphthalene-depleted (211 g), and oleylamine (111 g) is heated to 120° C. for 4 h, with distillative removal of volatile methanol while passing a nitrogen stream over. $^1$H NMR (CDCl$_3$; after removal of the solvent at 70° C. under high vacuum) confirms the amidation.

Inventive Example 4

In a 1 l jacketed vessel, a mixture of N-cocoylmorpholine (total amine number 207 mg KOH/g, 200 g), dimethyl oxalate (261 g) and isononanoic acid (9.2 g) is heated to 160° C. for 4 h. $^1$H NMR (CDCl$_3$) confirms the quaternization (δ=3.5 ppm, singlet, R$_3$NC$\underline{H}_3$). Subsequently, excess dimethyl oxalate is removed on a rotary evaporator at 120° C. under reduced pressure. The reaction product is dissolved in 2-propylheptanol (460 g) and heated to 120° C. for 6 h, with distillative removal of volatile methanol by passing a nitrogen stream over the mixture. The product is obtained as a solution in 2-propylheptanol.

C. Use Examples

In the use examples which follow, the additives are used as a pure substance or as a solution in a solvent.

Use Example 1: Determination of the Solubility and Formulation Properties

The compound according to comparative example 1: C12/14-NMe3-methyl oxalate is a crystalline solid and is insoluble in Solvent Naphtha at a concentration of 50% (w/w). The compound according to inventive example 1: C12/14-NMe3-2-propylheptyl oxalate is liquid and storage-stable at room temperature in 50% solution in Solvent Naphtha. This illustrates the significantly better handling properties of the inventive compound.

The following formulations were tested for storage stability at −20° C.:

a) 1:5 Dilution in Solvent Naphtha (5 Parts):

The following is observed:

Comparative example 1: solidification after 44 days at −20° C.

Inventive example 1: clear liquid after 60 days at −20° C.

b) 1:5:1 Dilution in 2-Ethylhexyl Nitrate (5 Parts) and Solvent Naphtha (1 Part)

The following is observed:

Comparative example 1: solidification after 1 day at −20° C.

Inventive example 1: clear liquid after 14 days at −20° C.

Use Example 2: Determination of Motor Oil Compatibility

Determination to standard DGMK 531 1-A with EN590 B7 fuel from Aral, unadditized, and Wintershall Multi-Rekord Top 15W-40 motor oil.

10 g in each case of motor oil and 10 g of the additive to be tested are weighed into a 500 ml Erlenmeyer flask and homogenized. The flask containing the mixture is loosely sealed with a glass stopper and conditioned in a drying cabinet at a temperature of 90±3° C. for three days. After the conditioning, the sample is cooled in a fume hood at room temperature for one hour. The mixture is then made up with 500 ml of diesel fuel and mixed thoroughly. A membrane filter of diameter 50 mm and pore size 0.8 μm is inserted into the filtration apparatus. Mixture is filtered through the membrane filter with the aid of a reduced pressure of 200 mbar. The filtration time is measured.

The following is observed:

Comparative example: very poor filterability, filtration time >300 sec. (fail)

Inventive example 1: good filterability, filtration time 114 sec. (pass)

Use Example 3: XUD9 Engine Test (Keep Clean)

Test according to above procedure CEC F-23-01 in Peugeot XUD9 engine. Aral EN590 B7 fuel, unadditized:

Test result (flow restriction with 0.1 mm needle stroke) for inventive example 1:

| Dosage [mg/kg] | Flow restriction |
| --- | --- |
| 0 | 76.8% |
| 24 | 46.6% |
| 36 | 14.5% |
| 48 | 4.5% |

The inventive compound is thus very effective with regard to prevention of deposits in indirect injection engines. The compound is also able to remove deposits present (clean-up effect).

Use Example 4: DW10 Zn Engine Test (Clean-Up)

The test was conducted with a Peugeot DW10 engine, which is used in CEC F-98-08 procedure, except that more severe conditions were used in the dirty-up part:

I. Dirty-up: the more severe conditions allow distinctly faster formation of injector deposits than under standard CEC F-98-08 conditions: The engine was operated at full load (4000 rpm) with EN590 B7 Aral, unadditized, containing 3 mg/kg Zn, for 4 h.

Test Result:

Under these conditions, the engine power was reduced from 96.4 kW to 92.1 kW after 4 h, corresponding to a power loss of 5.4%.

II. Clean-up:

CEC F-98-08 procedure shortened to 8 h, with 1 ppm Zn in EN590 B7 Aral, unadditized, containing 25 mg/kg active compound according to inventive example 1.

Test Result:

Engine power on commencement of test: 90.2 kW, after engine running for 3 h: 97.7 kW (i.e. full restoration of engine power)

The engine power remained constant at 97.7 kW until the end of the clean-up test, which lasted for 8 h.

The compound according to inventive example 1 (C12/14-NMe3-2-propylheptyl oxalate) has particular efficacy against deposits in direct injection engines. The compound shows high efficacy both in the prevention of buildup of deposits and in the removal of existing deposits.

Use Example 5: DW10 Na Soap IDID Test (Clean-Up)

To examine the influence of the additives on the performance of direct injection diesel engines, as a further test method, the IDID engine test was conducted, in which the exhaust gas temperatures in the cylinders at the cylinder outlet were determined on cold starting of the DW10 engine. (cf. method description above)

A DW10 direct injection diesel engine with common rail system from the manufacturer Peugeot was used, which was employed in the CEC F-098-08 test method. The method that was used derived from CEC F-098-08, with the difference that, rather than 1 ppm of Zn for artificial inducement of formation of deposits, 1 ppm by weight of sodium naphthenate and 20 ppm by weight of dodecenylsuccinic acid were used in each case. The fuel used was a commercial B7 diesel fuel according to EN 590 from Aral. The test duration is shortened to 8 hours compared to method CEC F-098-08. After respective DU and CU phases, the engine is cooled and then started at idling speed.

Test Results:

I. DU (dirty-up)

The exhaust gas temperatures of the 4 cylinders ("C1" to "C4") were measured at each of the cylinder outlets after 0 minutes ("ϑ0") and after 5 minutes ("ϑ5"). The results of the exhaust gas temperature measurements with average values ("Δ") and the greatest differences from Δ in the downward ("−") and upward ("+") directions for the two test runs are summarized in the following overview:

| ϑ0 | C1: 28° C. | C2: 27° C. | C3: 27° C. | C4: 26° C. |
| --- | --- | --- | --- | --- |
| ϑ5 | C1: 36° C. | C2: 68° C. | C3: 108° C. | C4: 121° C. |

Δ: 83° C. (−47° C./+38° C.)

A significant deviation from the mean of the exhaust gas temperatures and the significant differences between individual cylinders indicate the formation of IDIDs.

II. CU (clean-up) After the DU phase, the engine is operated with additized fuel without cleaning the injectors beforehand. The additization is effected with 70 mg/kg of active compound according to inventive example 1:

Again, the exhaust gas temperatures of the 4 cylinders ("C1" to "C4") were measured at each of the cylinder outlets after 0 minutes ("ϑ0") and after 5 minutes ("ϑ5"). The results of the exhaust gas temperature measurements with average values ("Δ") and the greatest differences from Δ in the downward ("−") and upward ("+") directions for the two test runs are summarized in the following overview:

| | | | | |
|---|---|---|---|---|
| 90 | C1: 28° C. | C2: 27°C. | C3: 27° C. | C4: 26° C. |
| 95 | C1: 78° C. | C2: 82°C. | C3: 77° C. | C4: 69° C. |

Δ: 77° C. (−8° C./+5° C.)

The deviation from the mean is insignificant; the IDIDs formed were removed.

The compound according to inventive example 1 (C12/14-NMe3-2-propylheptyl oxalate) has particular efficacy against IDID formation. The compound shows high efficacy both in the prevention of buildup of deposits and in the removal of existing deposits.

Use Example 6: DW10 Na Power-Loss Test (Keep-Clean)

To examine the efficacy of the inventive compounds against power loss caused by metals such as Na, K and others (and not by Zn as described above), an IDID engine test was used. During the run, the power is measured to CEC F-098-08.

| Test | Additive | Engine power before the test [kW] | Engine power after the test [kW] | Change in power in the test [%] |
|---|---|---|---|---|
| Keep-clean, 8 h | 1 ppm Na + 20 ppm dodecenylsuccinic acid | 97.8 | 91.9 | −6.0 |
| Keep-clean, 8 h | 1 ppm Na + 20 ppm dodecenylsuccinic acid and 150 ppm C12/14-NMe$_3$-2-propylheptyl oxalate | 96.4 | 96.6 | +0.2 |

The compounds according to this invention are effective against deposits of metals other than Zn in engines with direct injection, as shown in the above Na Power-loss Test. The compounds effectively prevent power loss and can also be used to remove deposits.

The disclosure of the publications cited herein is explicitly incorporated by reference.

The invention claimed is:

1. A fuel comprising an additive comprising a quaternized nitrogen compound,
   wherein the quaternized nitrogen compound is obtained by:
   a) reacting a quaternizable nitrogen compound comprising a quaternizable amino group with a quaternizing agent which converts the quaternizable amino group to a quaternary ammonium group, the quaternizing agent being a $C_1$-$C_4$-alkyl ester of an aliphatic, cycloaromatic or cycloaliphatic polycarboxylic acid, to obtain a quaternization product; and
   b) transesterifying or amidating a remaining ester group of the quaternization product, wherein:
   the quaternizing agent is an alkyl ester of an aliphatic, cycloaromatic or cycloaliphatic polycarboxylic acid;
   the transesterifying occurs with
      a saturated or unsaturated, linear, branched or cyclic, aliphatic $C_5$-$C_{28}$ mono-alcohol or polyol,
      a partly esterified polyol having at least one free hydroxyl group, or
      a polyisobutylene alcohol obtained by hydrofoimylating and reducing a polyisobutene, having a molecular mass ranging from 150 to 5000, found by gel permeation chromatography (THF solvent, polystyrene standard) of the polyisobutylene alcohol, or
   the transesterifying occurs by replacing a methyl or ethyl group in the remaining ester group of the quaternization product with a hydrocarbyl radical having 5 to 50 carbon atoms from a long-chain alcohol; and
   the amidating occurs with
      a saturated or unsaturated, linear, branched or cyclic, aliphatic, primary or secondary aliphatic $C_5$-$C_{28}$ mono- or polyamine, or
      a polyisobutyleneamine.

2. The fuel of claim 1, which is a diesel fuel.

3. The fuel of claim 1, which is a gasoline fuel.

4. A method of operating a gasoline engine, comprising providing the gasoline engine with the fuel of claim 3.

5. The method of claim 4, wherein the gasoline engine is a direct injection spark ignition (DISI) engine or a port fuel injector (PFI) engine.

* * * * *

UNITED STATES PATENT AND TRADEMARK OFFICE
CERTIFICATE OF CORRECTION

PATENT NO. : 10,815,444 B2
APPLICATION NO. : 16/453467
DATED : October 27, 2020
INVENTOR(S) : Markus Hansch et al.

It is certified that error appears in the above-identified patent and that said Letters Patent is hereby corrected as shown below:

Column 12, Line 33, "(Perauskas," should read -- (Petrauskas, --

Column 12, Line 57, "methylbehenylamine." should read -- methylphenylamine. --

Column 19, Lines 14-15, "co-polymers" should read -- copolymers --

Column 20, Line 17, "methyllaurylamines" should read -- methyllaurylamine --

Column 21, Line 31, "Tex." should read -- Texas. --

Column 22, Line 64, "hydroformylating" should read -- hydroformylation --

Column 24, Lines 57-58, "N,N-dimethyldimethylenetriamine," should read -- N,N-dimethylethylenediamine, --

Column 26, Line 49, "bishexamethylene- triamine" should read -- bishexamethylenetriamine --

Column 29, Line 25, "polyisobutylenesuccinic" should read -- polyisobutylene succinic --

Column 33, Line 20, "processability" should read -- processibility --

Column 34, Line 28, "polyalkenemono-" should read -- polyalkene mono --

Column 40, Line 37, "methylbehenylamine." should read -- methylphenylamine. --

Column 42, Lines 9-10, "dibehenylamine" should read -- diphenylamine --

Column 52, Claim 1, Line 7, "quatemizable" should read -- quaternizable --

Column 52, Claim 1, Line 12, "quatemization" should read -- quaternization --

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*

Column 52, Claim 1, Line 14, "quatemization" should read -- quaternization --

Column 52, Claim 1, Lines 21-22, "hydrofoimylating" should read -- hydroformylating --